(12) United States Patent
Bonitatibus et al.

(10) Patent No.: US 11,022,485 B2
(45) Date of Patent: Jun. 1, 2021

(54) SYSTEM, APPARATUS AND METHOD FOR IN SITU POLYCHROMATIC MEASUREMENT OF OPTICAL PROPERTIES OF TOPICALLY APPLIED SUNSCREEN

(71) Applicant: Solar Light Company, Inc., Glenside, PA (US)

(72) Inventors: Michael H. Bonitatibus, Glenside, PA (US); Curtis Cole, Glenside, PA (US)

(73) Assignee: SOLAR LIGHT COMPANY, INC., Glenside, PA (US)

( * ) Notice: Subject to any disclaimer, the term of this patent is extended or adjusted under 35 U.S.C. 154(b) by 0 days.

(21) Appl. No.: 16/565,602

(22) Filed: Sep. 10, 2019

(65) Prior Publication Data

US 2020/0018640 A1 Jan. 16, 2020

Related U.S. Application Data

(63) Continuation of application No. PCT/US2018/031320, filed on May 7, 2018.
(Continued)

(51) Int. Cl.
*G01J 1/42* (2006.01)
*G01J 1/02* (2006.01)
(Continued)

(52) U.S. Cl.
CPC .............. *G01J 1/429* (2013.01); *A61K 8/27* (2013.01); *A61K 8/35* (2013.01); *A61K 8/368* (2013.01);
(Continued)

(58) Field of Classification Search
CPC ........ G01J 1/429; G01J 1/0233; G01J 1/0407; G01J 1/08; G01J 1/18; A61K 8/27;
(Continued)

(56) References Cited

U.S. PATENT DOCUMENTS 3,397,022 A * 8/1968 Cole ..................... C03B 37/027
385/116
5,030,000 A * 7/1991 Kanda ................ A61B 5/14552
356/40

(Continued)

FOREIGN PATENT DOCUMENTS

WO 2017/067545 A1 4/2017

OTHER PUBLICATIONS

Stamatas et al., "Non-Invasive Measurements of Skin Pigmentation In Situ", Nov. 11, 2004, Pigment Cell Research, vol. 17, Iss. 6, pp. 618-626. (Year: 2004).*

(Continued)

*Primary Examiner* — David P Porta
*Assistant Examiner* — Jeremy S Valentiner
(74) *Attorney, Agent, or Firm* — Mark T. Vogelbacker; Eckert Seamans, Cherin & Mellott, LLC

(57) ABSTRACT

A system, apparatus and method of improved measurement of the SPF factor of sunscreen compositions. In one embodiment, a method of measuring the protection of a sunscreen composition includes exposing skin to a known intensity of light, measuring the amount of remitted light from the skin, applying sunscreen to the skin, exposing the skin to which the sunscreen has been applied the known intensity of emitted light of the spectrum of light from which the sunscreen is intended to protect the skin, measuring the amount of light remitted from the skin, and calculating a UltraViolet-A Protection Factor (UVA-PF) of the sunscreen by comparing the amount of light remitted from the skin with the sunscreen to the amount of light remitted from the skin without the sunscreen.

20 Claims, 19 Drawing Sheets

US 11,022,485 B2
Page 2

Related U.S. Application Data

(60) Provisional application No. 62/510,598, filed on May 24, 2017, provisional application No. 62/540,643, filed on Aug. 3, 2017.

(51) Int. Cl.

| | | |
|---|---|---|
| *G01J 1/08* | (2006.01) | |
| *A61K 8/27* | (2006.01) | |
| *A61K 8/35* | (2006.01) | |
| *A61K 8/368* | (2006.01) | |
| *A61K 8/40* | (2006.01) | |
| *A61K 8/41* | (2006.01) | |
| *A61Q 17/04* | (2006.01) | |
| *G01J 1/04* | (2006.01) | |
| *G01J 1/18* | (2006.01) | |
| *G01J 1/16* | (2006.01) | |
| *G01J 1/44* | (2006.01) | |

(52) U.S. Cl.
CPC ............... *A61K 8/40* (2013.01); *A61K 8/411* (2013.01); *A61Q 17/04* (2013.01); *G01J 1/0233* (2013.01); *G01J 1/0407* (2013.01); *G01J 1/08* (2013.01); *G01J 1/18* (2013.01); *G01J 2001/1673* (2013.01); *G01J 2001/4453* (2013.01)

(58) Field of Classification Search
CPC . A61K 8/35; A61K 8/368; A61K 8/40; A61K 8/411
See application file for complete search history.

(56) References Cited

U.S. PATENT DOCUMENTS

| | | | | |
|---|---|---|---|---|
| 5,569,923 | A | 10/1996 | Weissman et al. | |
| 5,625,459 | A | 4/1997 | Driver | |
| 5,640,957 | A * | 6/1997 | Kaminski | A61B 5/445 |
| | | | | 600/407 |
| 6,261,006 | B1 | 7/2001 | Selfridge | |
| 8,559,780 | B2 | 10/2013 | Bonitatibus | |
| 2002/0167667 | A1* | 11/2002 | Samsoondar | G01N 21/314 |
| | | | | 356/436 |
| 2008/0056995 | A1* | 3/2008 | Timmins | A61B 5/0059 |
| | | | | 424/9.2 |
| 2018/0321139 | A1* | 11/2018 | Helfmann | A61B 5/441 |

OTHER PUBLICATIONS

Newport, 77533 Bifurcated Fiber Optic Bundle, Core Diameter 4.5 mm, obtained Jul. 31, 2020 (inherency purposes) (Year: 2020).*
Mahadevan-Jansen et al., Development of a Fiber Optic Probe to Measure NIR Raman Spectra of Cervical Tissue In Vivo, Sep. 2008, Photochemistry and Photobiology, vol. 68, Iss. 3, pp. 427-431 (Year: 2008).*
Bevilacqua et al., In vivo local determination of tissue optical properties: applications to human brain, Aug. 1999, Applied Optics, vol. 38, No. 22, pp. 4939-4950 (Year: 1999).*
Reble, C., et al., "Evaluation of detection distance-dependent reflectance spectroscopy for the determination of the sun protection factor using pig ear skin", J. Biophotonics, vol. 11, article e201600257, May 18, 2017; pp. 1-10.
International Search Report for PCT/US18/31320, dated Sep. 25, 2018.
Written Opinion for PCT/US18/31320, dated Sep. 25, 2018.
Berger, D.S., "The Sunburning Ultraviolet Meter: Design and Performance", Photochemistry and Photobiology, vol. 24, No. 6, pp. 587-593, Dec. 1976.
Moyal, et al., "In Vivo Measurement of the Photostability of Sunscreen Products Using Diffuse Reflectance Spectroscopy", Photodermatology, Photoimmunology & Photomedicine, vol. 18, No. 1, pp. 14-22, Feb. 2002.
Ruvolo Jr, et al., "Diffuse Reflectance Spectroscopy for Ultraviolet a Protection Factor Measurement: Correlation Studies Between In Vitro and In Vivo Measurements", Photodermatology, Photoimmunology & Photomedicine, vol. 25, No. 6, pp. 298-304, Dec. 2009.
Anderson and Parrish, "The Optics of Human Skin", Journal of Investigative Dermatology, vol. 77, No. 1, pp. 13-19, Jul. 1, 1981.
Gillies, et al., "Non-Invasive In Vivo Determination of UVA Efficacy of Sunscreens Using Diffuse Reflectance Spectroscopy", Photodermatology, Photoimmunology & Photomedicine, vol. 19, No. 4, pp. 190-194, Aug. 2003.
"In Vitro Method for the Determination of the UVA Protection Factor and "Critical Wavelength" Values of Sunscreen Products", COLIPA: Auderghem, Belgium, pp. 1-29, 2011.
Ruvolo Jr, et al., "New Non-Invasive Approach Assessing In Vivo Sun Protection Factor (SPF) Using Diffuse Reflectance Spectroscopy and In Vitro Transmission", Photodermatology, Photoimmunology & Photomedicine, vol. 30, No. 4, pp. 202-211, Jan. 14, 2014.
Matts, et al., "The COLIPA In Vitro UVA Method: A Standard and Reproducible Measure of Sunscreen UVA Protection", International Journal of Cosmetic Science, vol. 32, No. 1, pp. 35-46, Jan. 13, 2010.
Gange, et al., "Action Spectra for Cutaneous Responses to Ultraviolet Radiation, The Biological Effects of UVA Radiation", Praeger Publishers. pp. 57-65, 1986.
Anders, et al., "Action Spectrum for Erythema in Humans Investigated With Dye Lasers", Photochemistry and Photobiology, vol. 61, No. 2, pp. 200-205, Feb. 1995.
Moyal, et al, "Determination of UVA Protection Factors Using the Persistent Pigment Darkening (PPD) as the End Point: (Part 1) Calibration of the Method", Photodermatology, Photoimmunology & Photomedicine, vol. 16, No. 6, pp. 246-249, Dec. 2000.
U. Utzinger, et al., Fiber optic probes for biomedical optical spectroscopy, J Biomed Opt. Jan. 2003;8(1):121-47.
Partial Supplemental European Search Report dated Dec. 10, 2020 issued in counterpart European Application No. 18806530.4.

* cited by examiner

SYSTEM, APPARATUS AND METHOD FOR IN SITU POLYCHROMATIC MEASUREMENT OF OPTICAL PROPERTIES OF TOPICALLY APPLIED SUNSCREEN

CROSS-REFERENCE TO RELATED APPLICATIONS

This application is a continuation of International Application No. PCT/US20018/031320, filed May 7, 2019 and titled "SYSTEM, APPARATUS AND METHOD FOR IN SITU POLYCHROMATIC MEASUREMENT OF OPTICAL PROPERTIES OF TOPICALLY APPLIED SUNSCREEN," which claims priority to U.S. Provisional Patent Application Ser. No. 62/540,643, filed Aug. 3, 2017, and entitled "System, Apparatus and Method for In Situ Measurement of Optical Properties of Topically Applied Sunscreen," as well as U.S. Provisional Patent Application Ser. No. 62/510,598, filed May 24, 2017, and entitled "System, Apparatus and Method for In Situ Measurement of Optical Properties of Topically Applied Sunscreen." The entire disclosures of which are herein incorporated by reference in their entirety.

BACKGROUND

The U.S. Food and Drug Administration (FDA) requires that sunscreen undergo clinical testing on humans to determine the strength of the protection provided by individual formulations. This testing requires that the humans be exposed to graded levels of broadband Ultraviolet (UV) simulated sunlight in two sites: one with the sunscreen on the skin and one without the sunscreen on the skin. The ratio of the exposure dose required to cause a sunburn reaction in the two sites (with and without the sunscreen) constitutes the Sun Protection Factor (SPF). The SPF is used to label the protectiveness of the sunscreen and allows consumers to choose between different protection levels depending on their individual needs.

The above-described testing requires multiple high intensity exposures to the test subjects (i.e., humans) in a procedure that may last several hours to complete in order to induce the sunburn reactions for high protection (i.e., SPF) sunscreens. There is measurable biological damage at the exposure sites at doses above and below the visible erythema endpoint beyond the skin reddening including DNA damage, increased enzymes that damage collagen and elastin, and immune cell destruction. Also, the exposed sites may exhibit marked pigmentation that may last for months in situations where exposures significantly exceed the minimal doses for erythema production.

Attempts to accurately measure the protectiveness of sunscreens using spectrophotometric methods, either by measuring dilute solutions of the sunscreens or thin films of sunscreens on artificial surfaces, instead of on humans, have failed to provide reliable predictive assessments of the SPFs. This is due primarily to the differences in the sunscreen optical properties on these artificial surfaces (or solutions) versus their behavior on human skin. Ultimately, skin is the ideal surface for testing sunscreens.

With the advent of broad spectrum sunscreen (i.e. those providing protection into the ultraviolet A—UVA range), it has also become important for manufacturers and consumers to know the level of protection provided by a sunscreen in the UVA portion of the UV spectrum.

Initial test procedures involved procedures similar to the SPF test described above, however using only the UVA portion of the UV spectrum to expose the human subjects. Similarly, prior art test procedures required long and extensive UV(A) exposures to human subjects in order to induce the biological endpoint (in this case immediate or permanent pigment darkening). The protection factor determined with this procedure was referred to as the UVA-PF(UltraViolet-A Protection Factor) or the PFA (Protection Factor in the UVA).

In the early 2000s, Diffuse Reflectance Spectroscopy (DRS) was introduced as a way to measure the UVA protectiveness of sunscreen products on human. This technique generally employs two scanning monochromators—one for illumination ("excitation") and one for measurement ("remitted"). The two monochromators are synced to each other and illuminate and measure at the same wavelength, in order to measure the transmission through the sunscreen film on the surface of the skin. Light from the "excitation" monochromator passes through the sunscreen on the surface of the skin, into the epidermal and dermal layers of the skin, and a portion of the light is then reflected and "remitted" back through the surface of the skin to be picked up by fiber optic bundles back to the "remitted light" monochromator and quantified with a photomultiplier tube. A diagram of the schematic is shown in FIG. 1. This measurement can be compared with a measurement made on a similar or the same patch of skin without the sunscreen to determine the SPF of the sunscreen.

In the prior art DRS method, since the photons pass through the sunscreen film two times, the transmission is calculated as the square root of the ratio of the "emitted" intensity divided by the "remitted" intensity.

$$T = \sqrt{I_{em}/I_{re}}$$

A full UVA spectral transmission scan is derived and is used to calculate the PFA of a sunscreen product using the persistent pigment darkening action spectrum and the emission spectrum of a solar simulator used in clinical testing. This is an improvement over clinical irradiation methods of the prior art, as the doses are a small fraction of that needed for clinical testing, and the speed required for assessment is increased while the time required for the assessment is reduced. No biological interaction or reaction is needed, as only the optical properties of the sunscreen on the surface are being interrogated by the light in the prior art DRS evaluation.

In a prior art DRS system, a bifurcated fiber optic bundle is used with randomized fibers separating illumination radiation and the returning diffuse reflected radiation. The typical fiber optic bundle can include quartz fibers 200 microns in diameter, one half used to illuminate the skin surface, and the other half to transmit the light reflected from within the skin back to a radiometric measurement device. The combined bundle of fibers randomly organized at the surface of the skin can be from 2 mm to 5 mm (or more) in diameter. The larger the bundle size, the greater the amount of signal that is provided to and from the skin sampling area.

The prior art DRS procedure requires the use of two expensive monochromators sync scanned in order to develop this full spectral assessment of the sunscreen. Use of sync scanning of two monochromators has several disadvantages. The first relates to the ability to input large amounts of "light" into the device as the entrance is typically a narrow slit, used to determine the potential resolution in wavelength units for each recorded scan measurement at a specified wavelength. A second limitation is the efficiency of the device in passing through the device with multiple reflections and internal slits to limit the amount of energy being passed to a narrow wavelength band. Efficiencies are low in order to define very precise and narrow wavelength bands with low stray light interference. Lamps with hundreds or thousands of watts are used to illuminate a double monochromator, with only a few milliwatts of defined monochromatic energy being passed through the entire system. DRS measurements using two double monochromator systems compound the inefficiencies in order to have very narrow monochromatic bands for the DRS measurements. Because the measurement requires taking the square root of the ratio of remitted/excitation irradiance, the overall dynamic range of the device is critically dependent on the amount of energy being available for the measurement. A third limitation is that since each wavelength is measured individually, the two monochromators must be scanned across the entire wavelength range, taking significant time to cover the entire range of measurements. A fourth limitation is that while DRS is a useful tool to evaluate UVA protection of sunscreens on human skin, it is limited in its scope to the range of approximately 320-400 nm as the inherent absorption properties of the skin (primarily stratum corneum and epidermis) severely diminish the amount of remitted photons in the range below 320 nm as they are irreversibly absorbed by proteins and DNA in the skin. Thus, the amount of available energy for measurement in the UVB range renders absorption measurements impossible.

Prior art DRS has also been employed to estimate sunscreen SPF values in a technique known as "Hybrid-DRS" SPF method, as described by Ruvolo et al. See Ruvolo E, Kollias N, Cole C., *New non-invasive approach assessing in vivo sun protection factor (SPF) using diffuse reflectance spectroscopy and in vitro transmission*. Photodermatology, Photoimmunology & Photomedicine. 30:4, 202-211, 2014. Using a separate in vitro spectroscopic scan of the sunscreen on an artificial substrate (e.g., a quartz plate, a polymethylmethacrylate (PMMA) plate, or VitroSkin™) a full range (290-400 nm) spectral scan of the shape of the absorbance of the sunscreen can be determined. While the absolute magnitude (height) of the scan is unreliable using this technique, the relative shape can be reliable for assessment of the protection of the UVB portion relative to the UVA portion. Ruvolo et al. used a mathematical technique to graft the UVB portion of the in vitro spectroscopic absorbance measurement onto the in vivo DRS absorbance spectrum using the overlapping spectra in the UVA range to properly scale the in vitro UVB absorbance portion of the spectrum to create a complete spectrum that accurately predicts SPF values of sunscreens.

SUMMARY

In one embodiment, an improved SPF measurement system, apparatus and method have been developed to evaluate sunscreen UVA protection in vivo, eliminating the need to irradiate human subjects to assess protection in the UVA portion of the ultraviolet spectrum. The presently disclosed technology is a simplified approach to measuring the UVA-PF as well as SPF protection of sunscreens that eliminates certain expensive optical equipment, and is much faster to conduct. In one embodiment, broad band UVA radiation can be directed onto a small area of human skin using a bifurcated fiber optic bundle, and the amount of reflected radiation remitted from the skin can be measured using a broad band UVA detector or sensor. Sunscreen can be applied to the test area and the measurement can be repeated. The UVA protection is easily calculated as the square root of the ratio of the two measurements. Use of a broad band exposure and radiation sensor in the presently disclosed technology eliminates the use of expensive and slow scanning monochromators used in traditional sync scanning methods reported in the literature for DRS evaluation of sunscreen protection. This data acquired via this technique can then be used to determine absolute SPF value of sunscreen products when combined with a full spectrum in vitro thin film spectroscopic scan of the test sunscreen.

In one embodiment, an improvement over prior art DRS systems is the efficiency at which the system or device of the presently disclosed technology receives light that returns to a sensor from the subject's skin due to an increased virtual aperture. The presently disclosed technology can employ at least two optical conduits with one or more common edges that constitute the active source and sensing element that contact at more than a single point along the extended edge of the source and the pickup conduits. Each optical conduit can be in direct contact with the patient's skin. This increased contact results in improved efficiency of receiving light remitted out of the subject's skin.

In one embodiment, which is an improvement over prior art DRS systems, the efficiency at which the system or device of the presently disclosed technology receives light remitted out of the subject's skin is substantially increased. The presently disclosed technology can employ at least two optical conduits in intimate contact with each other along a significant length which is also in contact with the skin. The length(s) of along which the conduits are in contact with each other and the skin constitute the active source and pickup element(s). This in an improvement over the fiber-based system of the prior art, because it greatly increases the total portion of skin generating remitted light. The fiber-based system of the prior art relies on a somewhat random arrangement of individual source and pickup fibers. Due to the very small diffusion distances in the skin, only a physically adjacent source and pickup fiber will constitute an active sensing element in the prior art system. Further, only the small area between the fibers constitutes the active measurement area in the prior art system. With a randomly mixed bifurcated fiber bundle, as is done in the prior art, the number of adjacent source and pickup fibers is a small fraction of the total fiber count resulting in a small total active contact area on the skin for all fibers. The increased sensor contact area on the skin of the present disclosure results in a substantial increase in intensity at the sensor of the light remitted out of the subject's skin.

The device of the presently disclosed technology can provide a low cost and simple tool to rapidly assess sunscreen efficacy without having long and laborious, skin damaging in vivo exposures to human subjects.

BRIEF DESCRIPTION OF THE SEVERAL VIEWS OF THE DRAWINGS

The foregoing summary, as well as the following detailed description of the presently disclosed technology, will be better understood when read in conjunction with the appended drawings. For the purpose of illustrating the presently disclosed technology, there are shown in the drawings various illustrative embodiments. It should be understood, however, that the presently disclosed technology is not limited to the precise arrangements and instrumentalities shown. In the drawings.

DETAILED DESCRIPTION

Figure 1:
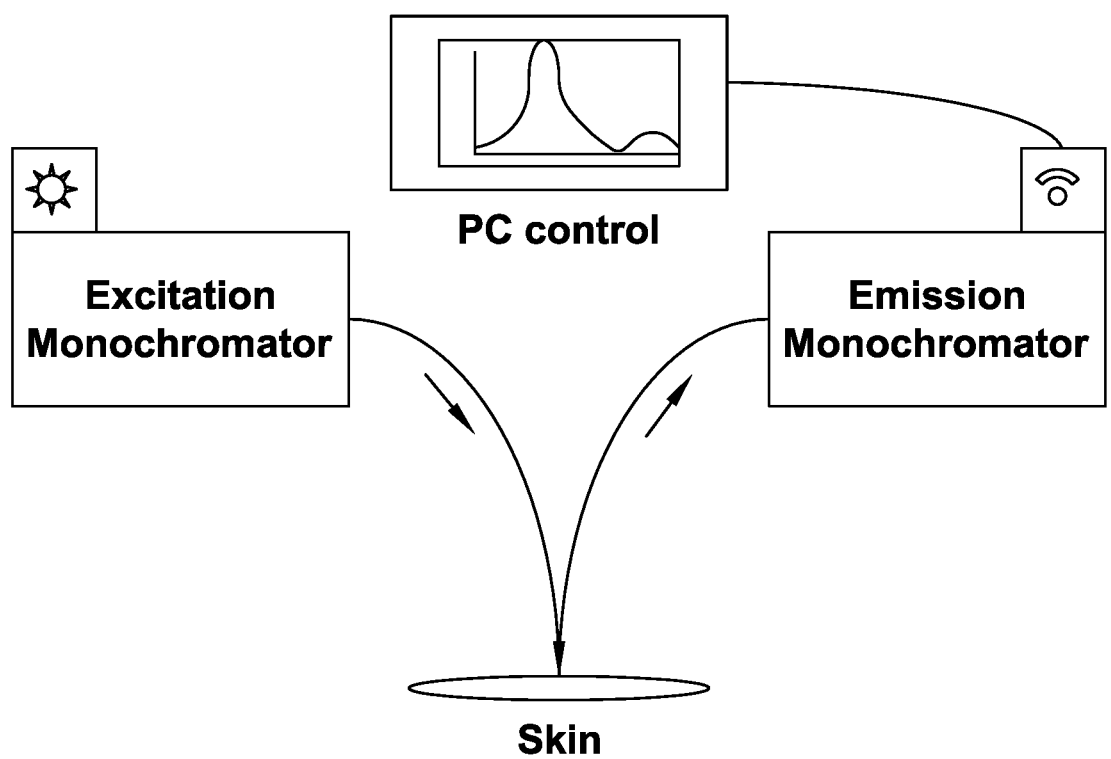
FIG. 1 is a schematic diagram showing a method of the prior art.

While systems, devices and methods are described herein by way of examples and embodiments, those skilled in the art recognize that the presently disclosed technology is not limited to the embodiments or drawings described. Rather, the presently disclosed technology covers all modifications, equivalents and alternatives falling within the spirit and scope of the appended claims. Features of any one embodiment disclosed herein can be omitted or incorporated into another embodiment.

Certain terminology is used in the following description for convenience only and is not limiting. The words "bottom," "top," "left," "right," "lower" and "upper" designate directions in the drawings to which reference is made. Unless specifically set forth herein, the terms "a," "an" and "the" are not limited to one element but instead should be read as meaning "at least one." As used herein, the word "may" is used in a permissive sense (i.e., meaning having the potential to) rather than the mandatory sense (i.e., meaning must). Similarly, the words "include," "including," and "includes" mean including, but not limited to. The terminology includes the words noted above, derivatives thereof and words of similar import. Any headings used herein are for organizational purposes only and are not meant to limit the scope of the description or the claims.

Referring to the drawings in detail, wherein like numerals indicate like elements throughout, FIGS. 2-11 illustrate a system, apparatus and method for improved DRS. The presently disclosed technology improves upon the prior art DRS technique at least by eliminating the need for the two monochromators and the time required to sync scan across the spectrum in order to determine the detailed full spectral transmission assessment at each wavelength. Instead of exposing the skin to individual wavelengths of the UVA spectrum as done in the prior art, in one embodiment of the presently disclosed technology the UVA spectrum of light from abroad band source (such as, but not limited to, a filtered xenon arc or tungsten lamp), can be used to illuminate the skin with the same bifurcated fiber optic bundle used in the known DRS measurement system. The remitted UVA radiation returns to a broad band UVA can be calculated as follows:

$$T = \sqrt{I_{em}/I_{re}}$$

In one embodiment of the presently disclosed technology, because the illuminating source is not required to pass through a monochromator to illuminate the skin, and a second monochromator to filter the remitted light, the sensitivity of the measurement radiometer can be greatly reduced, eliminating expensive electronics required for the measurement. Simple solid-state radiometric detectors and amplifiers can be utilized, replacing expensive and inefficient monochromator systems.

By shaping the "excitation" light source to have the same spectral proportions to the sources used in clinical PFA evaluations, and shaping the response spectrum of the sensor to be similar to the human Persistent Pigment Darkening (PPD) action spectrum, in one embodiment no further calculations or modifications are needed to determine the PFA of the sunscreen being tested. The measurement can be conducted in a short period of time (e.g., less than 10 seconds and, in one embodiment, significantly less than 2 seconds) as compared with prior art DRS spectral sync scans, which typically take a much longer time, such as 1-2 minutes.

In one embodiment, the presently disclosed technology improves upon the "monochromatic" approach by Ruvolo et al. by substituting the polychromatic DRS system described above. The presently disclosed technology can utilize the in vitro spectrum of the sunscreen determined with thin film spectroscopy, and the UVA-PF determined by the polychromatic DRS measurement to scale the in vitro absorbance spectrum until it matches the UVA-PF value determined by the DRS measurement. With this scaling and the full spectrum determined by thin film spectroscopy, the proper SPF value can be attained by the usual in vitro calculations as described in Matts et al. Matts P, Alard V, Brown M W, Ferrero L, Gers-Balag H, Issachar N, Moyal D, Wolber R, The COLIPA in vitro *UVA method: a standard and reproducible measure of sunscreen UVA protection*, Int. J. Cosm. Sci. 32(1) 35-46, 2010. The spectral shape is provided by the in vitro spectroscopic measurements, and the proper scaling of the spectrum is provided by the polychromatic DRS UVA-PF determination.

The presently disclosed system, in one embodiment, includes many of the same components used in the prior art DRS systems. However, one difference is that at or near the interface between the device and the subject's skin, one embodiment of the presently disclosed technology can include at least two optical conduits. The optical conduits can be in the form of rectilinear rods. Light pipe homogenizing rods utilize total internal reflection to homogenize non-uniform light sources regardless of their spectral characteristics. The optical conduits can be formed of any material that can transfer the light of interest (e.g., UV light). Examples of materials include quartz and fused silica. A suitable material can be anything that is highly transmissive. In one embodiment, more than two, such as eight, ten or even an odd number of optical conduits can be used. Every edge multiplies the remitted light signal by a factor proportional to the number of adjoining mating surfaces.

Figure 2:
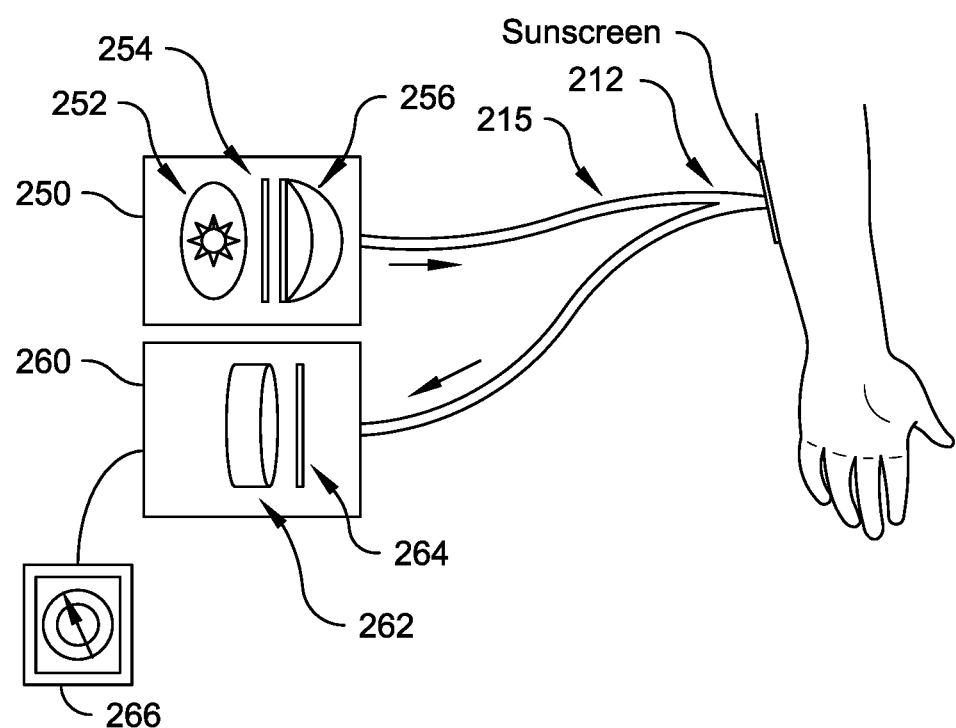
FIG. 2 is a schematic diagram showing an improved Diffuse Reflectance Spectroscopy system and method according to an embodiment of the present disclosure.
Figure 3:
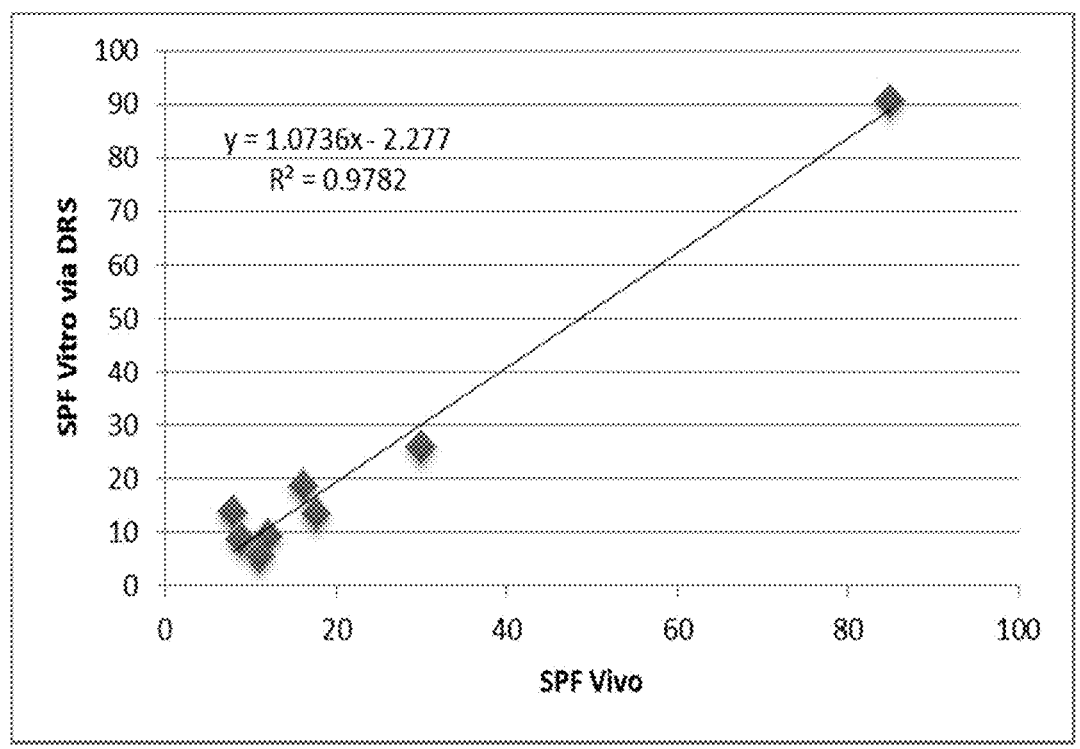
FIG. 3 is a graph charting testing of one embodiment of the present disclosure.
Figure 4:
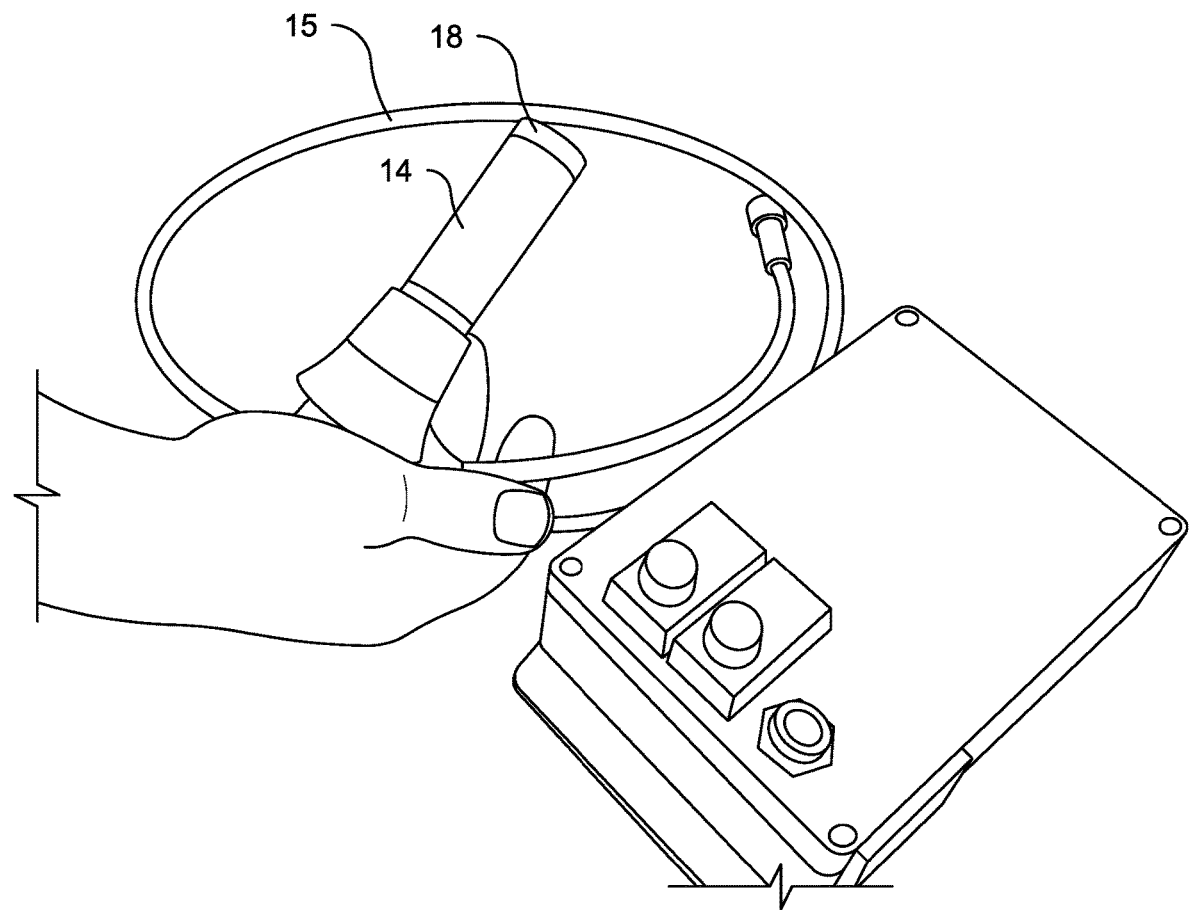
FIG. 4 is a perspective view of at least a portion of an improved DRS system according to an embodiment of the present disclosure.
Figure 5:
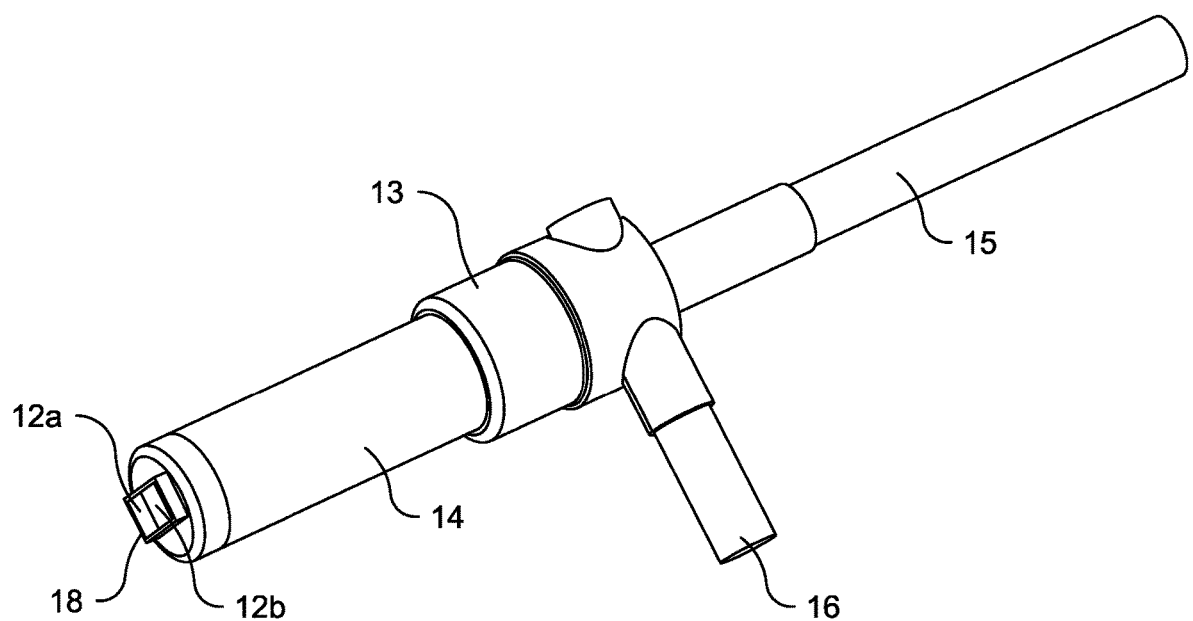
FIG. 5 is a perspective view of a portion of an improved DRS system according to an embodiment of the present disclosure.
Figure 6:
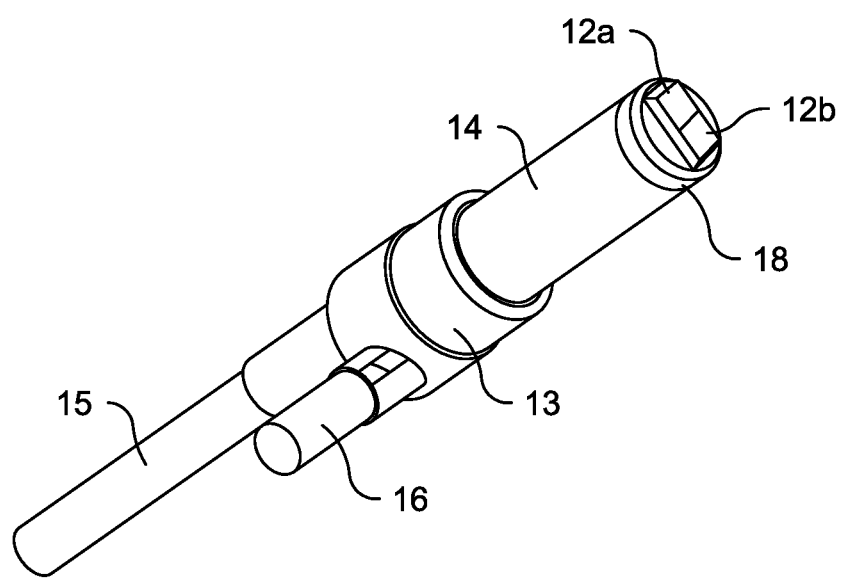
FIG. 6 is another perspective view of the device shown in FIG. 5.

A first end of each of the optical conduits can be connected to a fiber bundle or light feed, as used in the prior art DRS systems. As shown in FIG. 2, the fiber bundle 215 (e.g., a bifurcated fiber optic bundle) can, in turn, be connected to a first device 250 that can house one or more light sources 252 (e.g., a UVA source), one or more filters 254 and one or more lenses 256, for example, and a second device 260 that can house one or more sensors or detectors 262, one or more filters 264 (e.g., a shaping filter), and one or more measuring devices 266. An opposing second or free end of each optical conduit 212 is configured to directly contact the subject's skin and/or be positioned between the fiber bundle 215 and the subject's skin during testing. In operation, one of the optical conduits can direct incident light onto a portion of the subject's skin, and the other optical conduit can receive the reflected light from the subject's skin.

In one embodiment, each optical conduit can be a rod having at least one surface that faces, engages and/or complements a surface of another or the second optical conduit. These surfaces may be referred to herein as the "mating edge." This configuration allows a relatively large surface or edge of the optical conduits to be in abutting contact or at least facing one another. The shape and compactness of the optical conduits of the presently disclosed technology allows more light, which is initially directed to the subject's skin by the first or "excitation" optical conduit and reflected by the subject's skin, to be received by the second or "remitted light" optical conduit. This proximity and configuration of the optical conduits allows for increased light reception by the device as compared to prior art DRS systems that use a fiber optic bundle to receive the reflected light.

Figure 15:
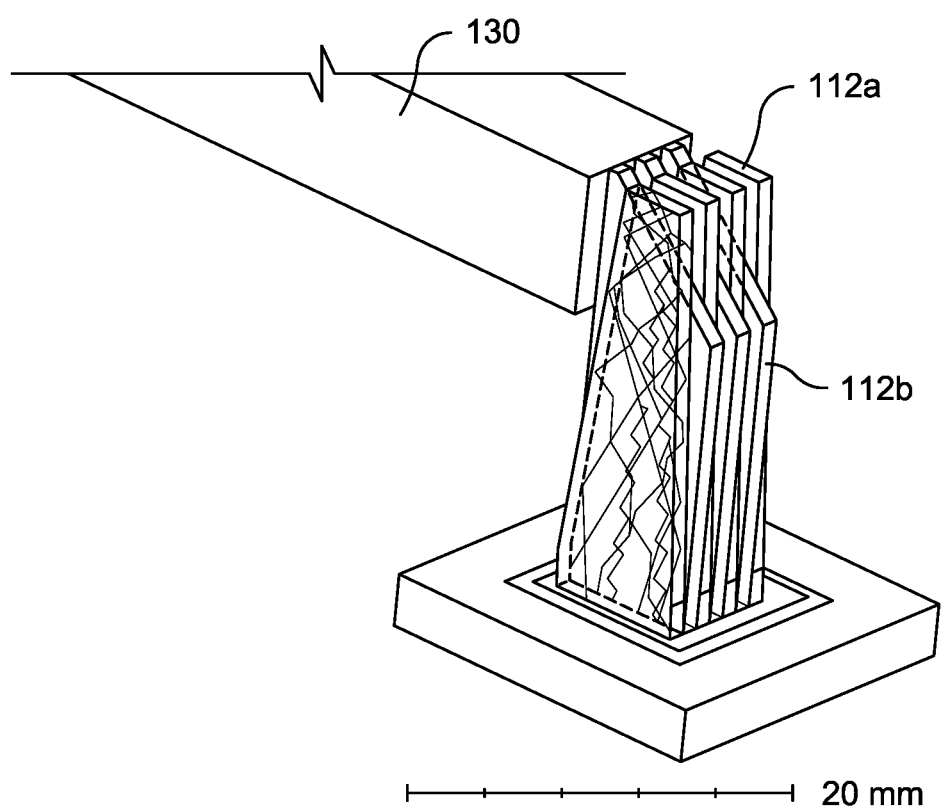
FIG. 15 shows a stack of alternating "sliver" shaped emission and remission conduits according to one embodiment of the present disclosure.
Figure 16:
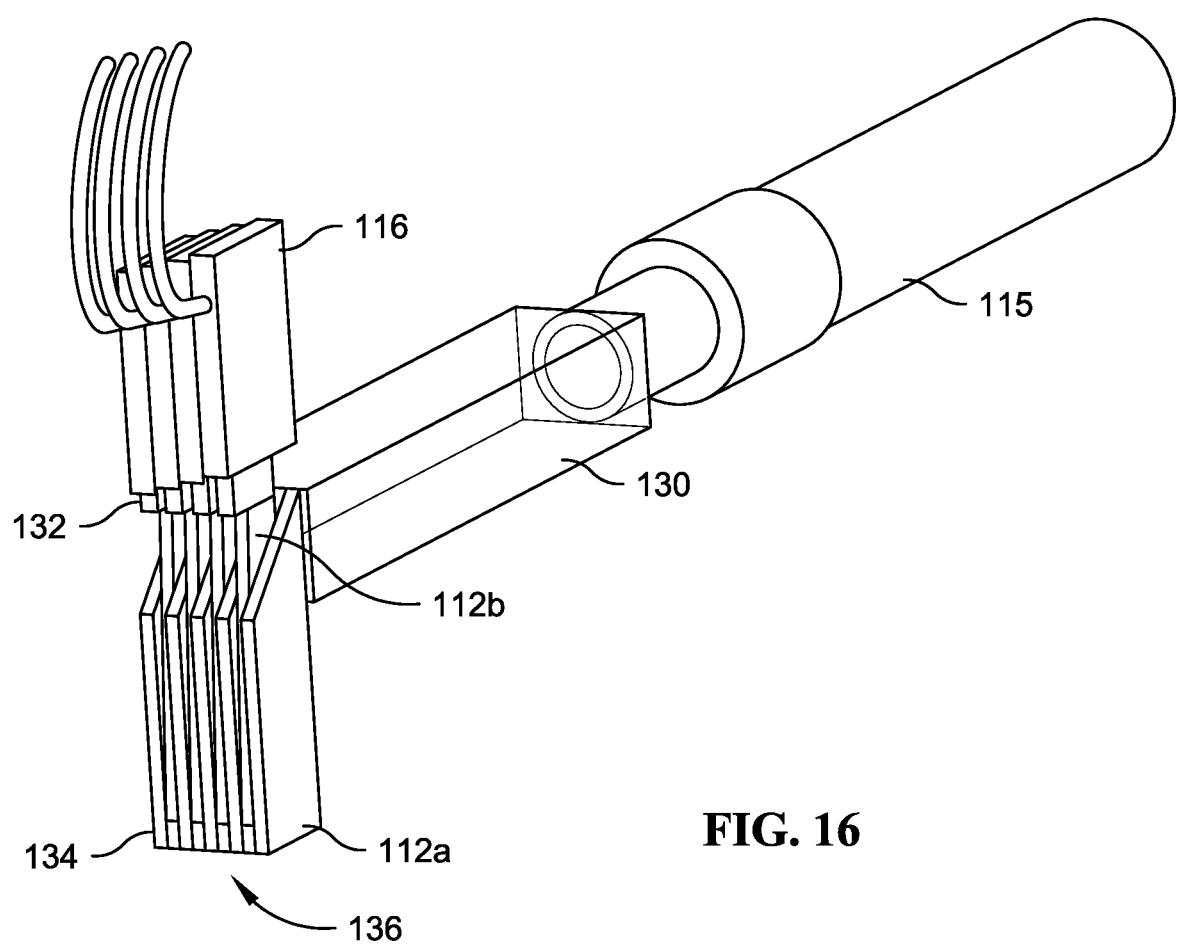
FIG. 16 shows another embodiment of the stack shown in FIG. 15.
Figure 17:
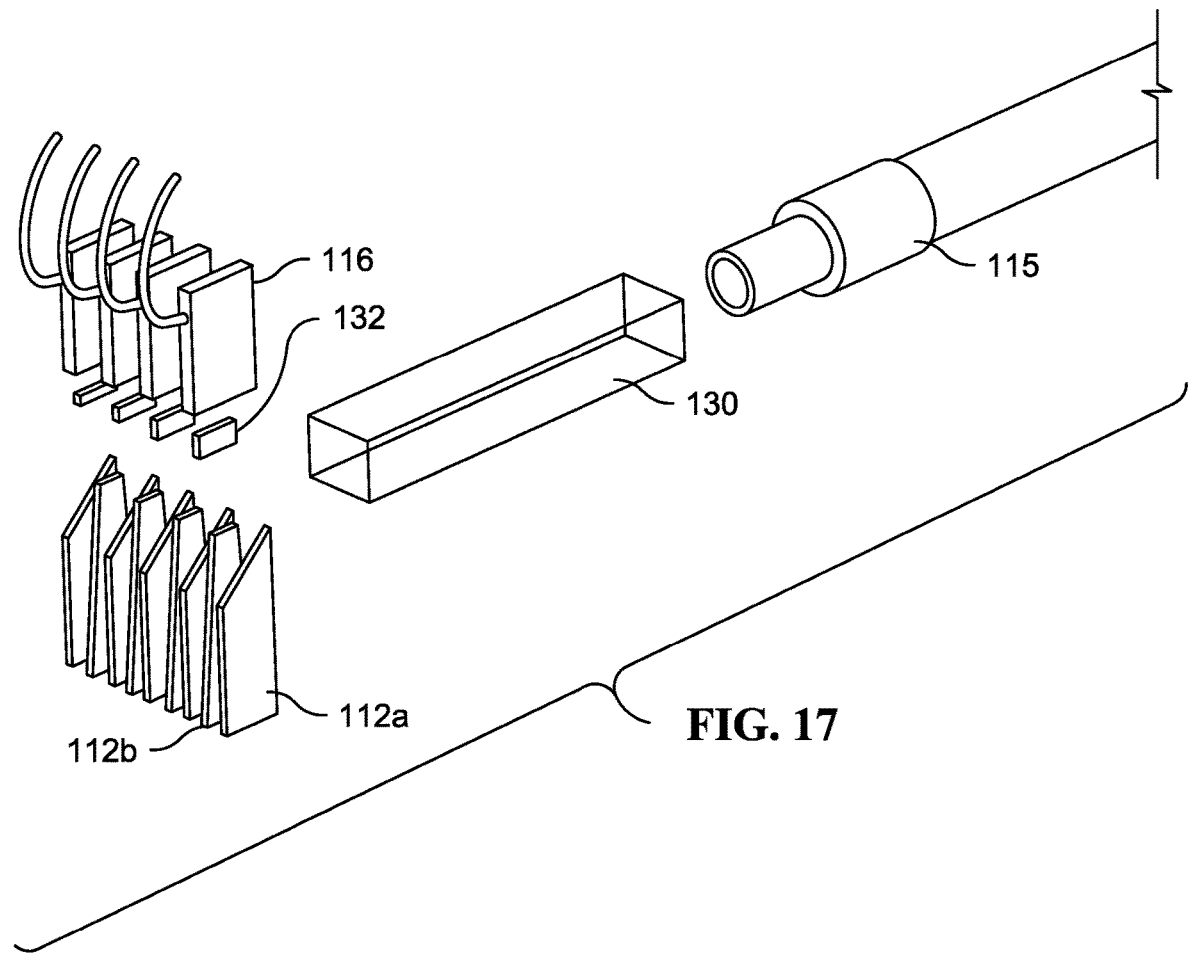
FIG. 17 shows a partially exploded view of FIG. 16.

For example, in one embodiment of the presently disclosed technology, each optical conduit can have a rectangular (e.g., right rectangular prism) shape so that a flat surface of each optical conduit is in abutting contact with (or at least facing) a flat surface of the other optical conduit (see, e.g., FIGS. 4-9B). As another example of the presently disclosed technology, one of the optical conduits can have a concave surface, while the other optical conduit can have a complementary convex surface. The concave and convex surfaces can be in abutting contact or at least facing one another. As a further example, each optical conduit can have a cross-sectional shape of a pentagon, a hexagon, an octagon or any other shape with at least one substantially flat or planar surface. In yet another embodiment, the conduits are cylindrical, one contained within the other and in contact at their respective inner and outer surfaces. In another embodiment of the presently disclosed technology, a stack of alternating "sliver" shaped emission and remission conduits can be employed to increase the length of adjoining surfaces, such as shown in FIGS. 15-17. The above-described arrangements provide for increased surface area contact or exposure between the optical conduits.

In one embodiment, each optical conduit can have a width of approximately 8 mm and a length of approximately 8 mm. However, optical conduits of other widths and lengths could function in a desirable manner. Optionally, conduits in contact with each other along a width of at least 2.0 mm can be employed. In certain instances, conduits in contact with each other along a width of at least 4.0 mm are even more preferred. These optical conduits typically include a coating that provides Total Internal Reflection (TIR) of light in the conduit. Optionally, and preferably in certain instances, this coating (and any protective layer) is the only separation between the light paths in the conduits. Optionally, this separation can be approximately 10-40 microns, with a separation in the range of 10-20 microns being preferred. The coating(s) can be formed of materials conventionally used in the art.

In contrast, in prior art DRS systems, the optical fibers of the fiber bundle each have a circular shape, and at best each optical fiber only contacts another one of the optical fibers at a point or a line, not an entire surface. The use of the fiber bundle in prior art DRS systems is inefficient due to the circular shape and configuration of the optical fibers, as only a small or inefficient amount of the light emitted from one or more of the optical fibers of the prior art DRS system is received by adjacent optical fibers.

Figure 7:
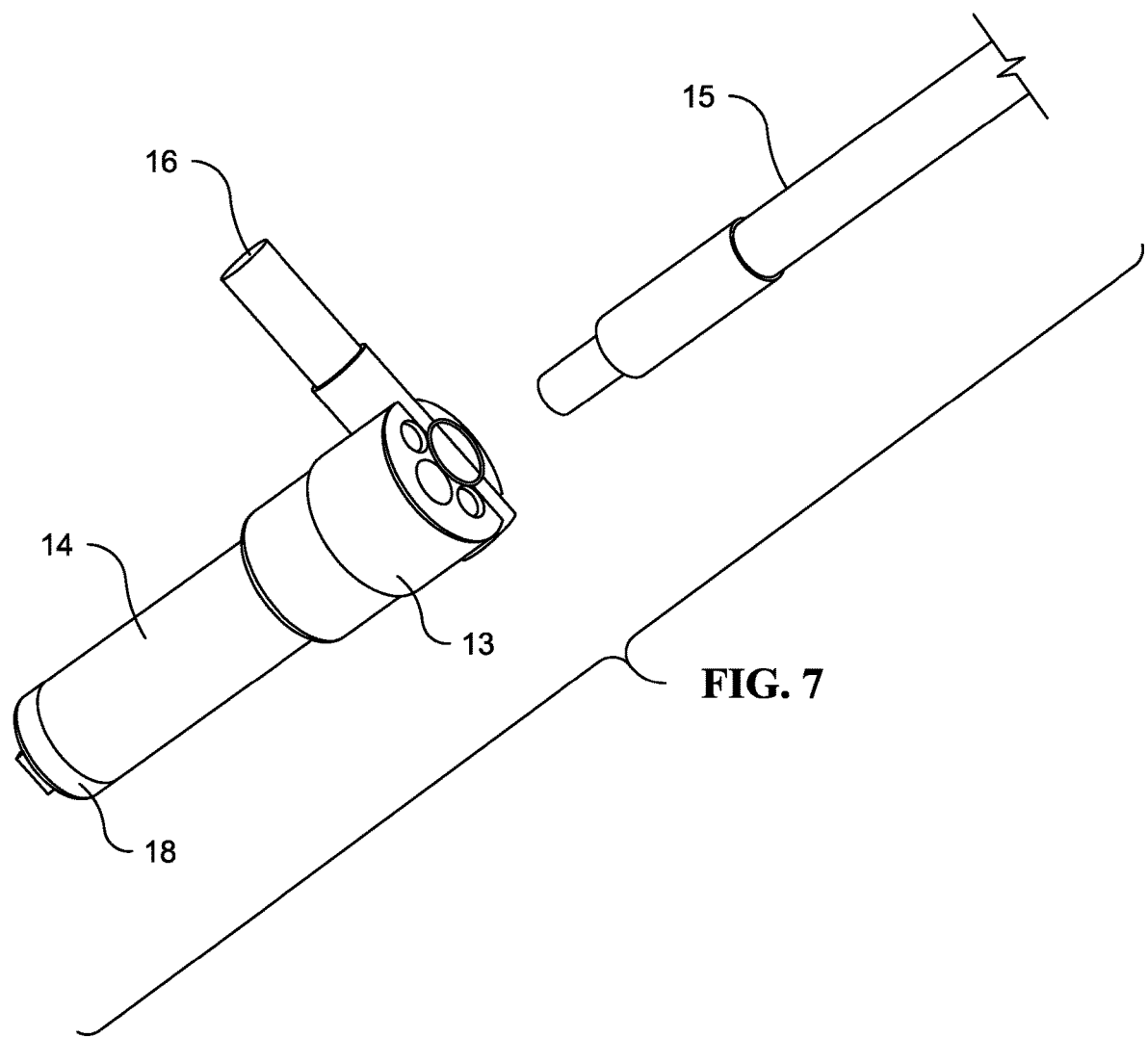
FIG. 7 is a partially exploded view of a portion of the device shown in FIG. 5.

As shown in FIGS. 4-9B, in one embodiment of the presently disclosed technology, at least two optical conduits, generally designated 12a and 12b, can be positioned (at least partially or entirely) within a cover sleeve 14. A hub 13 can include a first end with a radially outwardly receptacle to receive at least a portion of the cover sleeve 14, and one or more radially inwardly receptacles to receive at least a portion of each optical conduit 12a, 12b. A photomultiplier (PMT) light sensor or light detector 16 can be attached to the hub 13. A light feed, fiber bundle or input light guide 15 can operatively connect the optical conduits 12a, 12b to a light source and/or a measurement device. More particularly, an opposing second end of the hub 13 can include a receptacle to receive at least a portion of the light feed 15. As shown in FIG. 7, the light feed 15 can be removably attached to the hub 13. An end fitting 18 with a raised lip that surrounds a portion of the optical conduits 12a, 12b can attach to the cover sleeve 14. At least a portion of the raised lip of the end fitting 18 can contact the subject's skin 20 during use or testing. A light filter 22, a stop capsule 24, two or more light seals 26, each optionally in the form of an O-ring, and a molded light gasket 28 can be positioned within the hub 13 between the light feed 15 and the optical conduits 12a, 12b.

Figure 12:
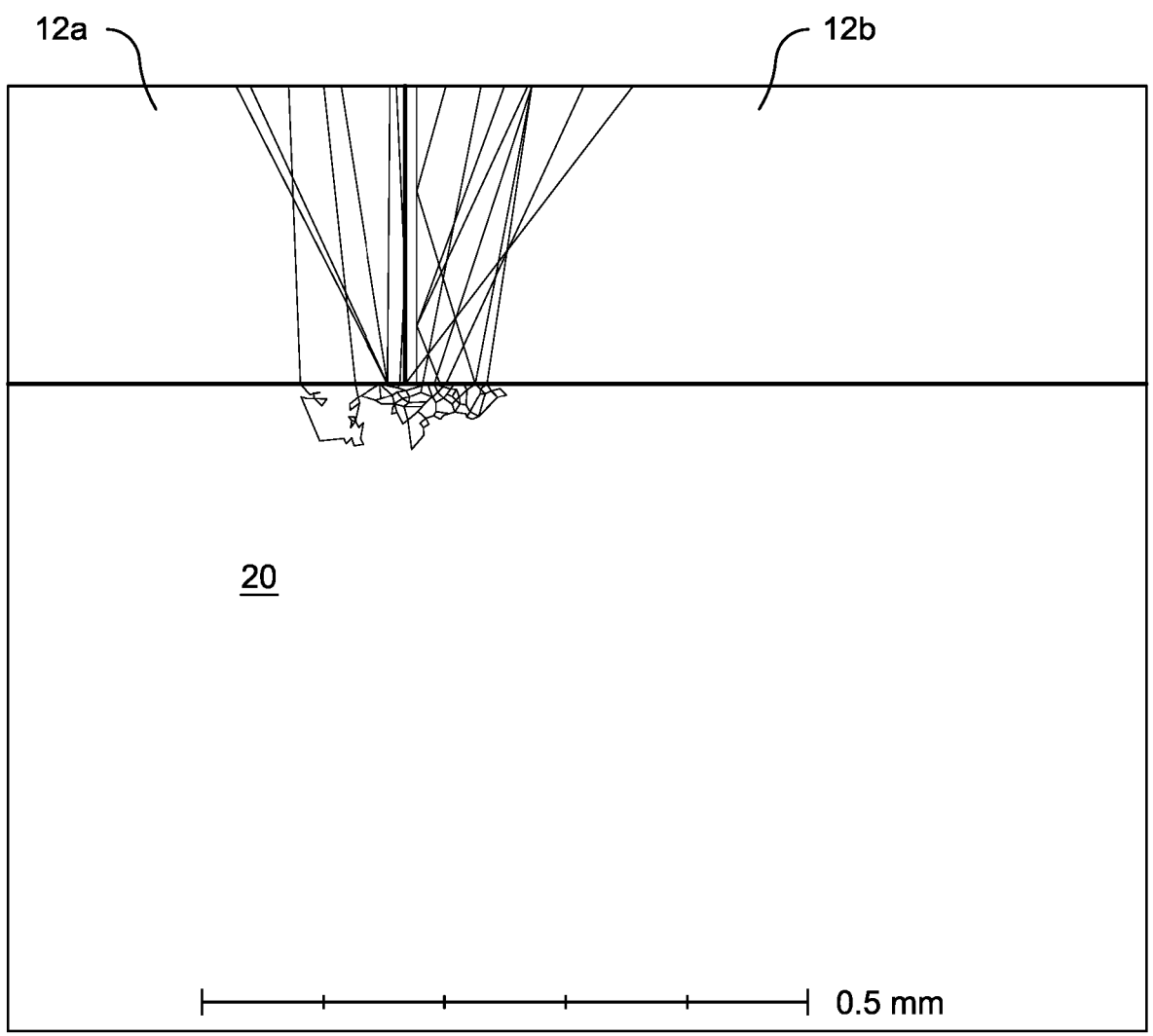
FIG. 12 is a model of internal skin diffusion using the device shown in FIG. 5.
Figure 13:
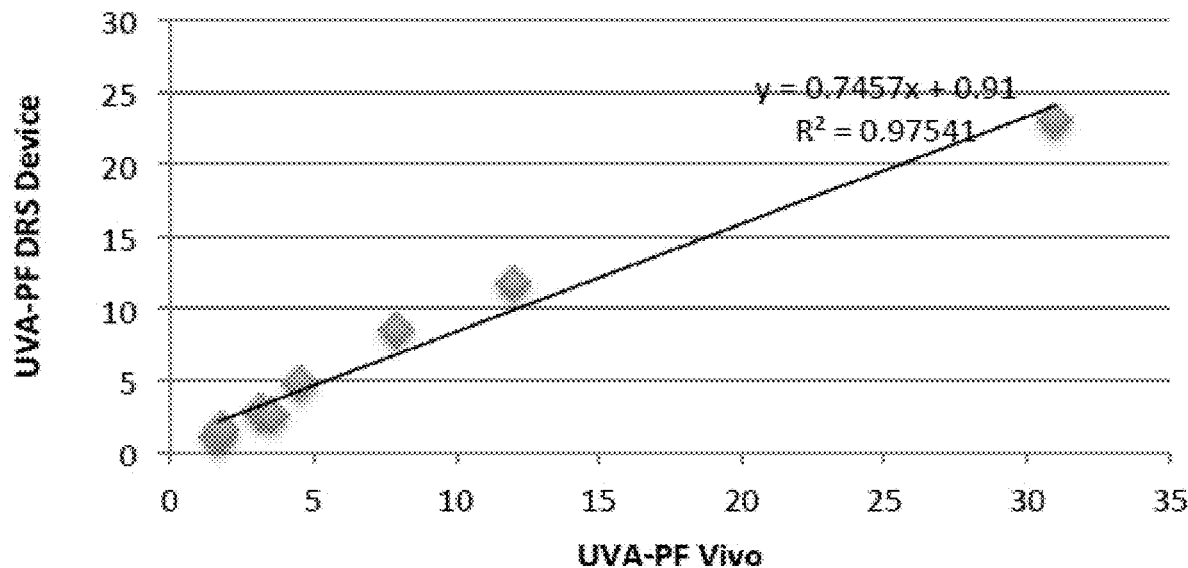
FIG. 13 is a graph charting UVA protection factor to compare the presently disclosed technology with in vivo testing.
Figure 14:
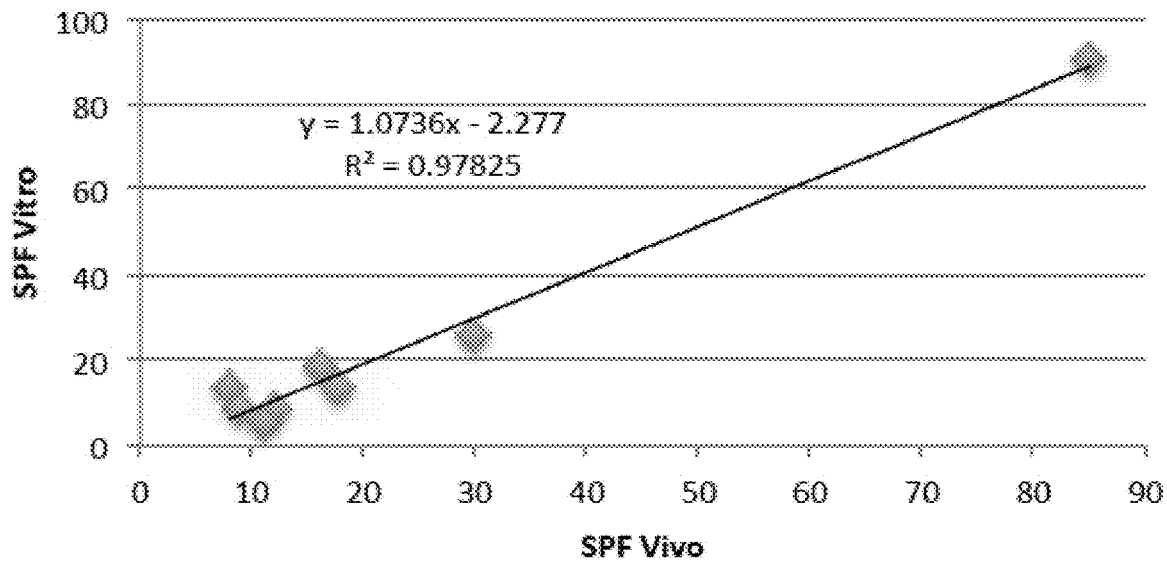
FIG. 14 is a graph charting predictions for SPF to compare the presently disclosed technology with in vivo testing.

FIG. 12 shows an internal skin diffusion model according to one embodiment of the present disclosure. The bottom area or rectangle is representative of skin that services as bulk scatter material with 0.01 mm mean path length. In operation, light in source rod enters from the upper left in FIG. 12, enters the skin and is diffused internally. Remitted light is picked up along line on mating rod edge. Remitted light is captured in rod 12b and transmitted to one or more photomultiplier (PMT) sensors.

As shown in FIGS. 15-17, in certain embodiment of the presently disclosed technology, a plurality of conduits are employed. Each remission conduit 112b can be positioned between two emission conduits 112a, and a variety of different options exist for the numbers of each conduit 112a, 112b. In particular, in one option (see FIG. 15), four emission conduits 112a (e.g., "source slivers") and three remission conduits 112b are used. In another option (see FIGS. 16 and 17), five emission conduits 112a and four remission conduits 112b are used. Alternatively, the device can include three emission conduits 112a and two remission conduits 112b. A homogenizer 130, such as a homogenizer rod, can be attached or operatively connected to a first or proximal end of each of the plurality of conduits 112a, 112b. An input light guide 115 can be attached or operatively connected to an end of the homogenizer 130 opposite the plurality of conduits 112a, 112b. As shown in FIGS. 16 and 17, one or a plurality of PMT light detectors 116 can be used. Optionally, four light detectors 116 can be attached to or operatively connected to the first or proximal end of the remission conduits 112b, or a single PMT detector 116 can be operatively connected to the first or proximal end of the remission conduits 112b. One or more filters 132 (e.g., spectral filters) can be positioned between each corresponding light detector 116 and remission conduit 112b. One or a plurality of moisture seals 134 can be located at or near a second or distal end of each of the plurality of conduits 112a, 112b. The second or distal end of each of the plurality of conduits 112a, 112b is the output/input face 136 of the device.

Test Data: Eight sunscreens of known SPF value were tested using one embodiment of the polychromatic DRS system described herein. Determination of both the SPF and the UVA-PF can be derived solely from the polychromatic DRS UVA-PF measurement, and a separate in vitro thin film spectroscopic scan. The amount of UVA light remitted from the skin was measured with the polychromatic DRS device. The sensitivity of the photomultiplier was adjusted at each site by adjusting the high voltage to achieve as high a signal that is possible yet below the saturation level of the photomultiplier. Remitted intensity at each of three sites for each of the eight sunscreens was recorded. The sunscreens were then applied at a density of 2 mg/cm² (standard dosage rate) and allowed to dry for 15 minutes. The remitted light was measured in triplicate and recorded at each of the sunscreen sites.

Separately, the in vitro absorbance of each of the sunscreens was measured on polymethylmethacrylate (PMMA) plates before and after UV irradiation (to account for non-photostable sunscreen behavior—see Ruvolo et al. discussed above). The absorbance after the UV exposure was adjusted according to the magnitude of the UVA-PF to match the polychromatic UVA-PF DRS measurement. This resulting adjusted absorbance spectrum was then used to calculate the predicted SPF value of each of the sunscreens.

The discussion below shows how the SPF data for each of several sunscreens tested using the system and method of the presently disclosed technology.

Materials: Eight sunscreen products were chosen for the test evaluations that cover a diversity of sunscreen filter compositions and SPFs. These would be considered to cover the extremes of the types of filter combinations available commercially. These eight sunscreens have known UVA-PF and SPF values. The composition of these sunscreens were as shown in Table 1 below:

TABLE 1

| Treatment Code | UV filter composition | SPF | UVA-PF |
|---|---|---|---|
| J | 10% Octocrylene, 6% oxybenzone, 5% octyl salicylate, 3% avobenzone | 30 | 12 |
| A | 7% Padimate O, 3% Oxybenzone | 16.2 | 3.2 |
| I | 6% Octinoxate, 4% Zinc Oxide | 11.1 | 8 |
| G | 7% Octinoxate, 3% Avobenzone | 12 | 4.6 |
| F | 5% Oxybenzone | 9 | 3.6 |
| E | 7% Octinoxate | 8 | 1.7 |
| H | 20% Zinc Oxide | 17.7 | 1.8 |

TABLE 1-continued

| Treatment Code | UV filter composition | SPF | UVA-PF |
|---|---|---|---|
| K | 10% Homosalate, 5% octisalate, 3% avobenzone, 2.8% octocrylene, 6% oxybenzone | 85 | 31 |

These sunscreens were manufactured under GMP conditions and comply with permissible FDA concentrations and combinations according to the FDA 2011 Sunscreen Monograph for sunscreen products.

Ten test subjects were recruited based on FDA Sunscreen Monograph testing criteria, having skin phototypes I, II, or III, with no disqualifying skin conditions or markings.

Baseline Measurements: The Individual Typology Angle (ITA) angle of the skin (measurement of the skins' darkness) was measured with a Minolta Chromameter at each sunscreen application site (test site). Each test site was marked with a surgical marker having an area of 3×10 cm². The device according to the presently disclosed technology was placed on the surface of the skin at each treatment site, and the High Voltage setting was adjusted to yield a reading of 12V (just below saturation at 14V). Three measurements were then made within each test site using the device and recorded for the baseline measurements.

Sunscreen Application: The sunscreen treatment sites were randomized for each subject and given a unique treatment code. Sunscreens were applied at 2 mg/cm² to the test area by "dotting" the area with sunscreen formulation, and gently spreading the sunscreen over the entire test area for approximately 20 seconds. A minimum of 15 minutes elapsed before initiating further measurements.

Test Measurements: Before measurements were conducted in each of the treatment sites, the fiber optic probe was cleaned with alcohol and clean paper Kimwipe™. The high voltage setting was adjusted at each treatment site to the setting recorded during the baseline measurement. The probe was placed onto the skin and held until stabilization of the signal, and the stable signal value was recorded. Three measurements were conducted within each sunscreen treatment area. After completing measurements at each sunscreen site, the fiber optic probe was again cleaned with alcohol and Kimwipe™ before starting the next treatment site. These measurements were used in Ruvolo E, Kollias N, Cole C., *New non-invasive approach assessing in vivo sun protection factor (SPF) using diffuse reflectance spectroscopy and in vitro transmission*. Photodermatology, Photoimmunology & Photomedicine. 30:4, 202-211, 2014.

Clinical Observations: There were no visual skin changes after measurements were made with the device.

In Vitro Sunscreen Measurements: Thin film spectroscopic measurements were conducted on the test sunscreens using double-grating spectrophotometer. Sunscreens were applied to polymethymethracrylate (PMMA) plates at 1.3 mg/cm² and allowed to dry in a dark area for at least 15 minutes before absorbance measurements. Four plates were prepared for each test sunscreen, and one absorbance measurement was conducted for each plate with a spectrophotometer. The plates were exposed to broad spectrum UV radiation (UVB+UVA) The exposure dose for each sunscreen series was calculated as 1.2 J/cm² UVA*the UVA-PF observed by diffuse reflectance measurements. Sunscreen absorbance on the plates was measured after the prescribed UV dose had been accumulated.

Computations: Sunscreen absorption measurements from the in vitro PMMA plate scans, pre- and post-UV exposure were made. Averages were computed at each wavelength for each sunscreen across the four plates. The UVA source spectrum of the multiport was cross multiplied by the spectral response spectrum of the device photosensor system and integrated to represent a baseline measurement. This spectrum was then modified by the in vitro absorbance spectrum of each sunscreen ($I_{pre}=I*10^{(-A_{pre}*f)}$), where A is the measured absorbance value of the sunscreen at each wavelength, and f is a scalar value to be determined. This sunscreen modified spectrum was integrated over the wavelengths and the resulting value was divided into the baseline measurement to determine the $UVA_{IV}$-PF in vitro Protection Factor. Using the Excel "Goal Seek" function, the value of "f" is set by matching this $UVA_{IV}$ Protection Factor to the UVA-PF observed from the clinical measurements of the sunscreen using the "device". This scalar value "f" is then used to scale the post-UV in vitro sunscreen absorbance values to yield the final scaled "post-UV" sunscreen absorption spectrum $A_{final}=(A_{post}*f)$). This final scaled post-UV sunscreen absorption spectrum was then used to calculate the sunscreen SPF and UVA-PF using standard clinical solar simulator spectra with the CIE erythema action spectrum, and the Persistent Pigment Darkening (PPD) action spectrum (as per ISO 24443). These values were then compared against the in vivo clinical results for these sunscreens and correlations determined.

Results: ITA° vs High Voltage Setting

There was a notable correlation of the high voltage setting of the device with the ITA° of the test sites. Higher ITA° (lighter colored skin) required lower HV settings to attain the baseline signal setting of 12V. See FIG. 18.

Figure 18:
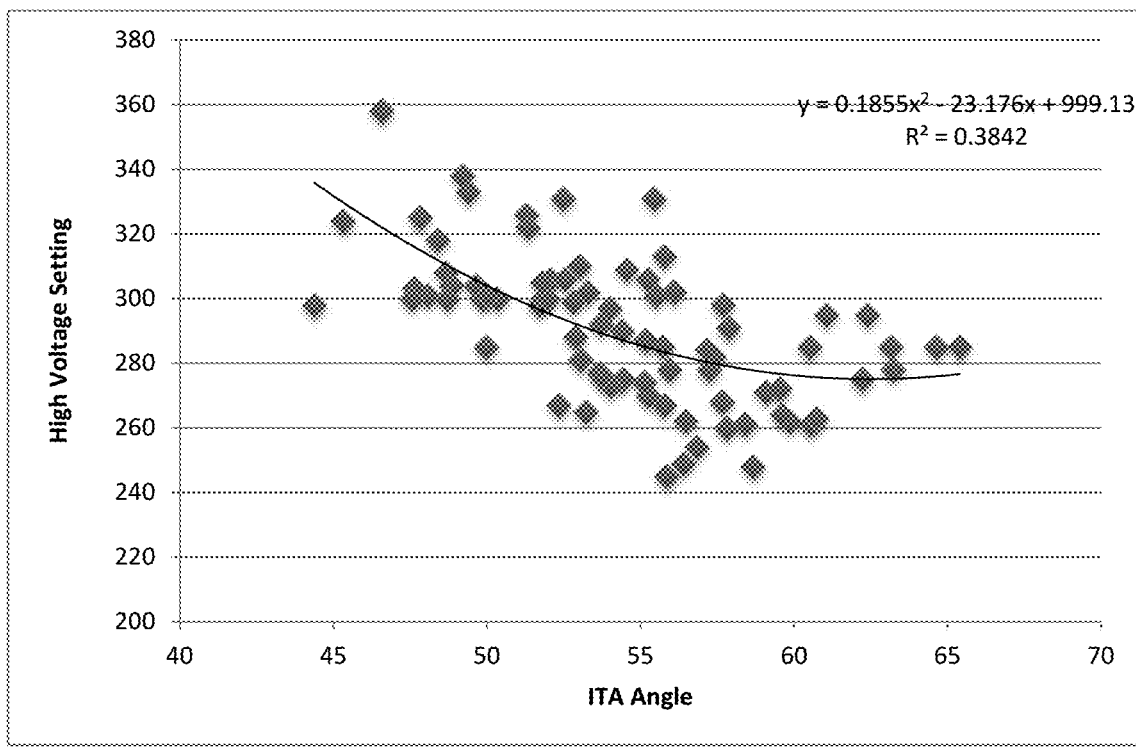
FIG. 18 is a graph depicting the results of one embodiment of the present disclosure.

FIG. 18 shows the relationship between unprotected MED values for sunscreen test subjects and their ITA° as published by others.

SPF determinations: The UVA-PF ratios determined on these same sunscreens were very similar to those observed in a preliminary (n=1) evaluation, as shown in Table 2 below:

TABLE 2

| Sunscreen Code | Prelim POP Device UVA-PFs | Clinical POP Device UVA-PFs |
| --- | --- | --- |
| A | 2.9 | 3.05 |
| E | 1.15 | 1.35 |
| F | 3.8 | 3.81 |
| G | 21.9 | 18.1 |
| H | 15.9 | 13.8 |
| I | 4.2 | 3.20 |
| J | 20.7 | 18.8 |
| K | 26.7 | 22.7 |

SPF values calculated using the clinical device derived UVA-PFs (above) and the in vitro absorbance measurements and presented in Table 3 below:

TABLE 3

| | In Vivo (Prior Art) SPF Measurement | SPF By the Method of the Invention |
| --- | --- | --- |
| A | 16.2 | 18.8 |
| E | 8 | 25.9 |
| F | 9 | 8.5 |
| G | 12 | 16.1 |

TABLE 3-continued

| | In Vivo (Prior Art) SPF Measurement | SPF By the Method of the Invention |
| --- | --- | --- |
| H | 17.7 | 12.6 |
| I | 11.1 | 11.8 |
| J | 30 | 26.2 |
| K | 85 | 77.1 |

Figure 19:
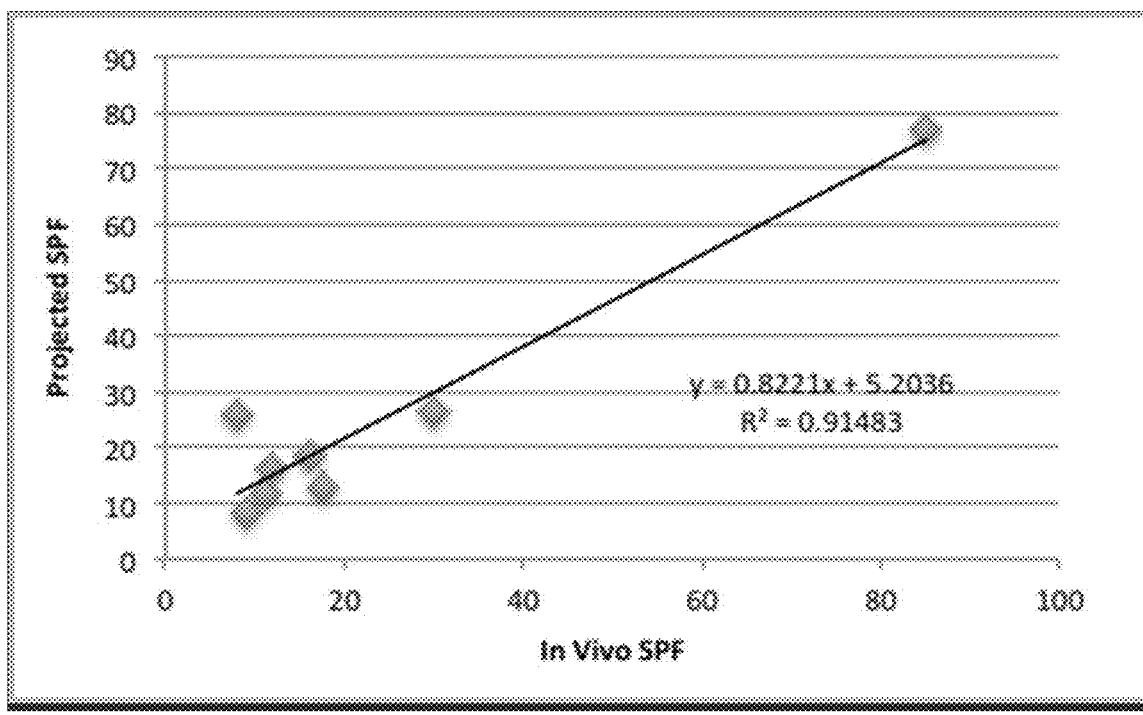
FIG. 19 is a graph depicting the results of one embodiment of the present disclosure.

These results are in close agreement with the preliminary POP evaluation, as shown in FIG. 19.

Where $R^2$ is the first order linear fit of the indicated line equation.

Figure 20:
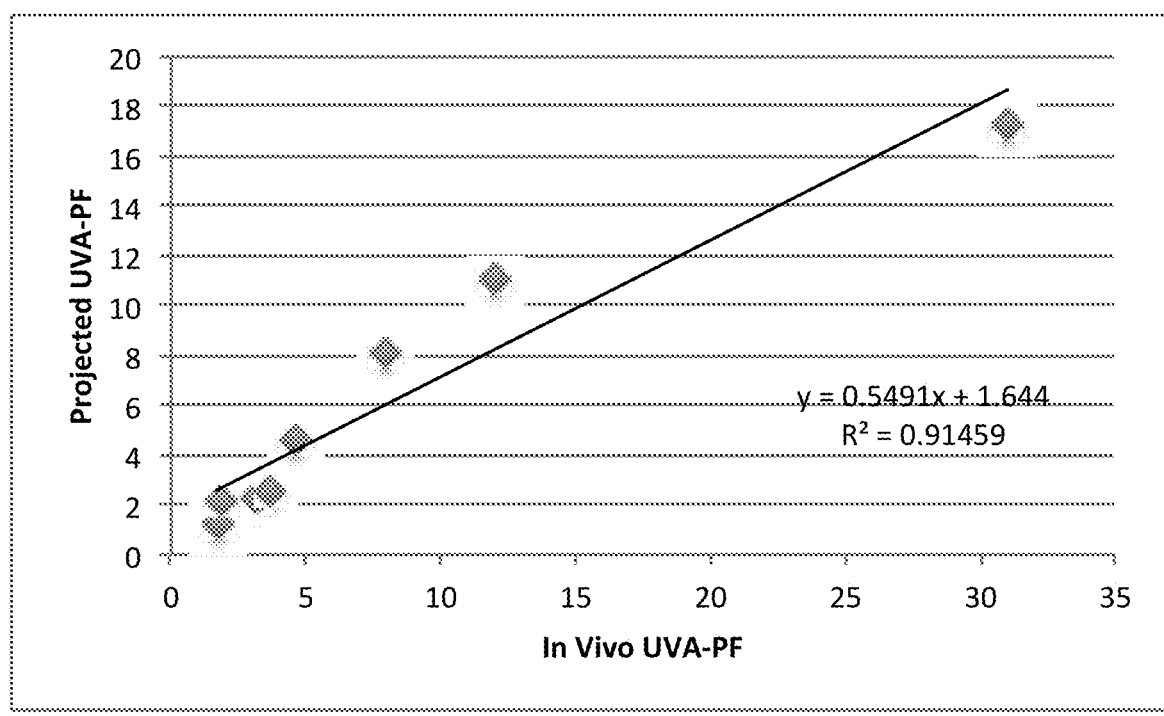
FIG. 20 is a graph depicting the results of one embodiment of the present disclosure.

UVA-PF Evaluations: Using the same scaled post-UV exposure absorbance curves to estimate SPF values, combined with the PPD action spectra and clinical UVA simulator spectrum, UVA-PF values were calculated. Determinations were again made using the two spectrophotometer devices. The results are shown in Table 4 below (as well as in FIG. 20):

TABLE 4

| | In Vivo (Prior Art) UVA-PF | UVA-PF By the Method of the Invention |
| --- | --- | --- |
| A | 3.2 | 2.3 |
| E | 1.7 | 1.25 |
| F | 3.6 | 2.53 |
| G | 4.6 | 4.61 |
| H | 7.97 | 8.1 |
| I | 1.81 | 2.2 |
| J | 12 | 11.1 |
| K | 31 | 17.3 |

Projected UVA-PF using A Device According to the Presently Disclosed Technology: Clinical testing of the device according to the presently disclosed technology yielded SPF projections and UVA-PF values with high correlation with in vivo test results with high correlation factors ($R^2>0.91$), and also similar to the preliminary testing (n=1). The slope was also close (=0.82) to the ideal slope of 1, meaning 1:1 correspondence of the projected SPF value and the true in vivo SPF value.

These data are indicators that the device according to the presently disclosed technology with a broad band diffuse reflectance measurement device approach can be used to provide predictive SPF and UVA-PF values for sunscreen products when used in conjunction with full UV spectrum (UVB+UVA) in vitro spectroscopic measurements.

Data obtained from this device can be used to calculate the degree of protection provided by sunscreen compositions. These calculations can be performed in a variety of known ways. For example, E. Ruvolo et al, *New noninvasive approach assessing in vivo sun protection factor (SPF) using diffuse reflectance spectroscopy (DRS) and in vitro transmission, Photodermatol Photoimmunol Photomed* 2014 Vol. 30; 4, pp. 202-211.

Sun protection factors may also be calculated by constructing the photodetector in such a way that its responsiveness to remitted light mimics the biological responsiveness of skin to the various portions or wavelengths of light that are of interest. This eliminates the need to conduct measurements of the amount of remitted light at each of the various portions or wavelengths of light, weight them according to the biological responsiveness of skin to the various portions or wavelengths of light, and then execute calculations based on that weighting.

It has long been known that the biological responsiveness of skin to light is different for each of the various portions or wavelengths of light to which it can be exposed. This biological responsiveness can be stated in terms of the amount of light required to induce skin redness (erythema) or skin darkening (pigmentation or melanogenesis), typically as the median dose required to produce this effect in a population. Because the skin in some populations (e.g. fair skinned persons) is more responsive to light and more likely to exhibit erythema than others, it is sometimes advantageous to measure these effects in populations classified according to skin type, such as according to the well-known Fitzpatrick Scale. These data, which are often presented in the form of responsiveness or sensitivity curves, are found in the literature. For example, Gange, R. W. et al, *Action spectra for Cutaneous Responses to Ultraviolet Radiation*, The biological effects of UVA radiation. F Urbach, R W Gange eds, Praeger Publishers, New York N.Y., 1986, pp. 57-65; Anders, A. et al., *Action Spectrum For Erythema In Humans Investigated With Dye Lasers*, Photochemistry and Photobiology, Vol. 61, No. 2, pp. 200-205, (1995). The responsiveness of skin to the various portions or wavelengths of light to which it can be exposed is a crucial factor in calculating SPF or UVA Protection Factor (UVA-PF) and must be taken into account. Moyal, D. et al. *Determination Of UVA Protection Factors Using The Persistent Pigment Darkening (PPD) As The End Point*, Photodermatol Photoimmunol Photomed, Vol. 16: pp. 245-249 (2000).

Conventionally, reflectance spectroscopic measurements of SPF have accounted for responsiveness of skin to the various portions or wavelengths of light to which it can be exposed by passing remitted light through a device (e.g. a diffraction grating or monochromator) that breaks the remitted light into a spectrum. Measurements are then made of the amount of remitted light in each of the various portions or wavelengths of remitted light. These measurements are then weighted in accordance with the skin responsiveness data mentioned above, and the SPF is then calculated. This method, while workable, requires a great deal of calculation to accomplish the weighting. It also requires the use of monochromators or similar devices to expose the spectrum of remitted light, and this is expensive, mechanically complex, and limits the amount of available illumination light (and hence the remitted signal) available for the measurement due to the inefficiency of the throughput of monochromator systems. This limits the available range of measurements possible by the system. It also introduces "noise" to the remitted light, to the detriment of measurement.

In an aspect of the presently disclosed technology, a spectral analysis and spectral weighting according to the biological responsiveness of skin to light is different for each of the various portions or wavelengths of light to which it can be exposed can be eliminated, along with the costly, noise-producing hardware required for that weighting. Instead, the photodetector that receives the remitted light is modified so that its sensitivity to remitted light in the range of interest approximates or matches the biological responsiveness of skin to that light. That is to say, the sensitivity of the photodetector over this range is made to approximate or match the responsiveness or sensitivity curve of skin. This may be done so as to match the sensitivity or responsiveness curve with respect to erythema, pigmentation, or a combination of them. When the photodetector is so configured, it is possible to simply use a measurement of the total remitted light detected by the photodetector in that region with and without the sunscreen on the skin in order to calculate the UVA-PF and furthermore having a separate spectral scan of the absorbance of the sunscreen, the SPF can be calculated using conventional computations.

Figure 8:
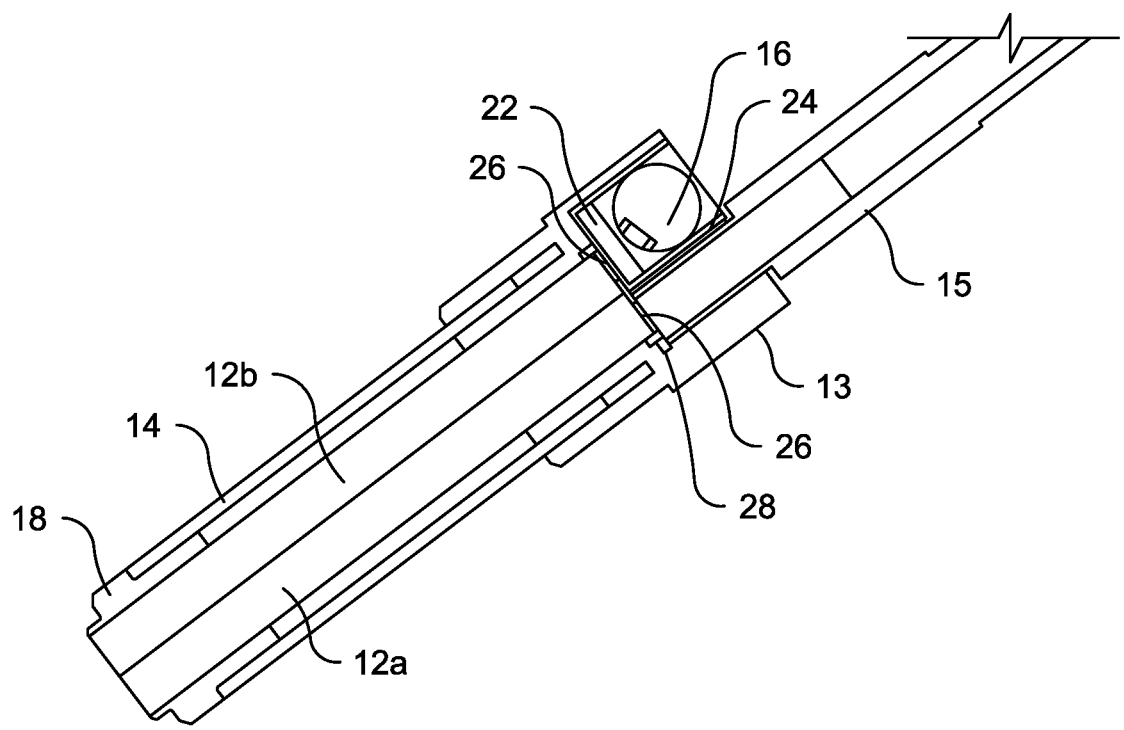
FIG. 8 is a cross-sectional view of a portion of the device shown in FIG. 5.
Figure 9A:
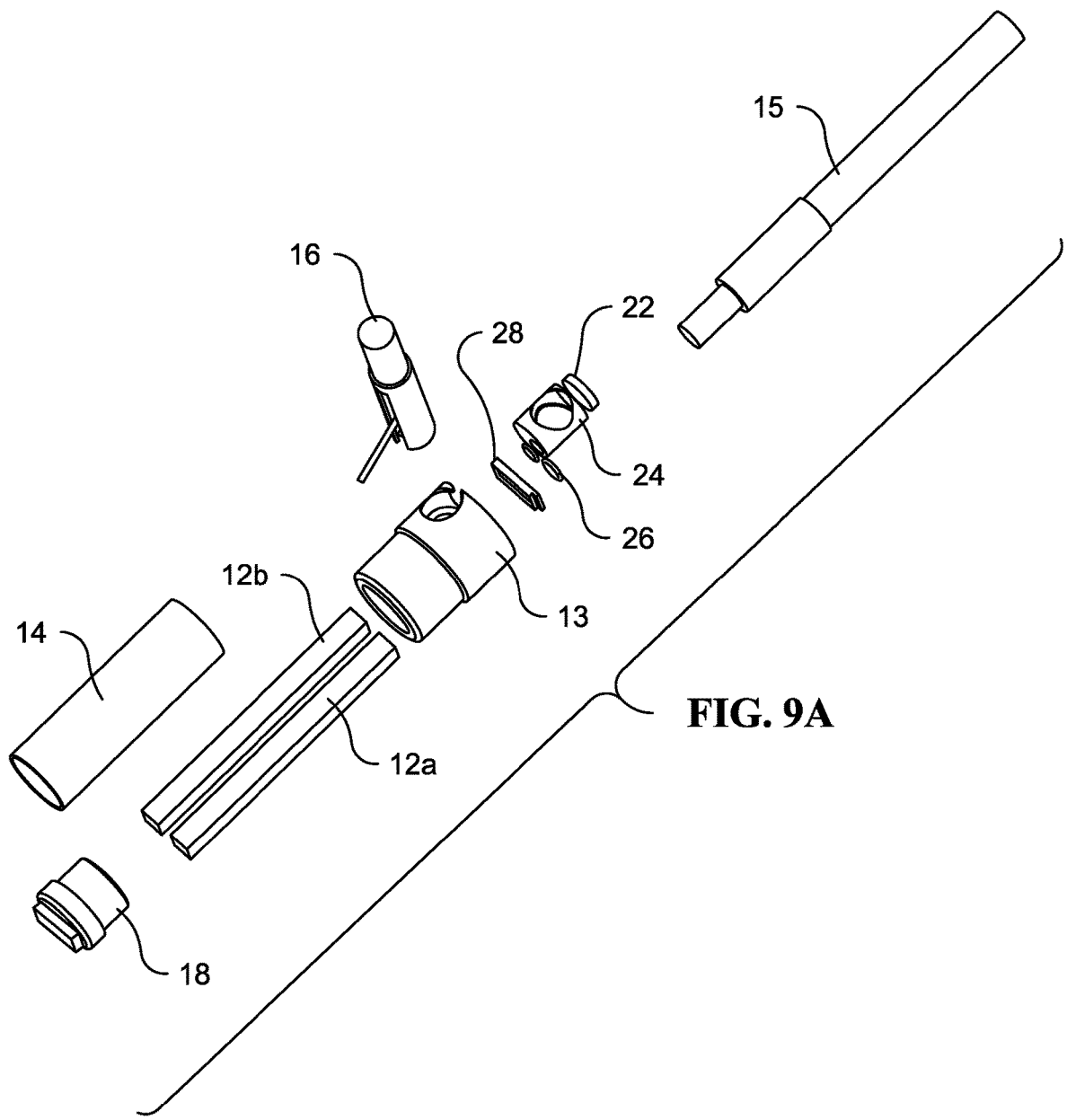
FIG. 9A is a partially exploded view of at least a portion of the device shown in FIG. 5.
Figure 9B:
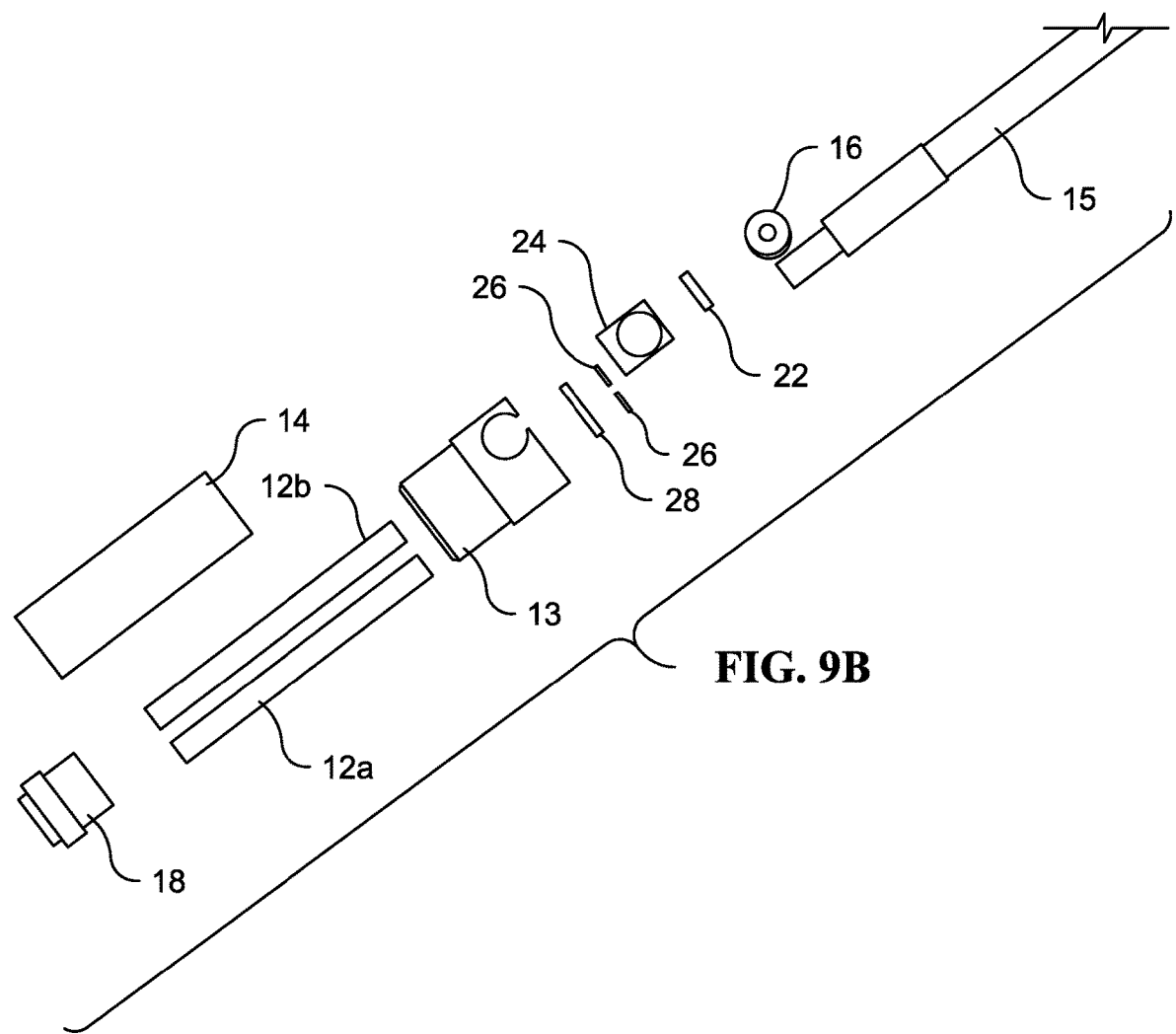
FIG. 9B is another partially exploded view of at least a portion of the device shown in FIG. 5.
Figure 10:
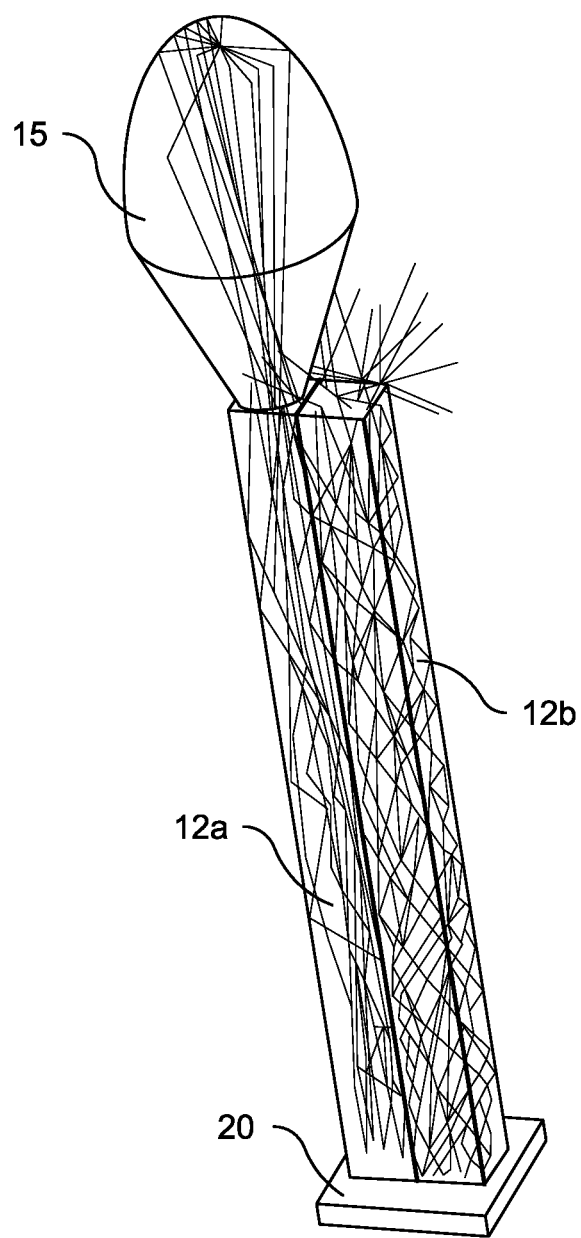
FIG. 10 is a schematic view of the device shown in FIG. 5 in operation.
Figure 11:
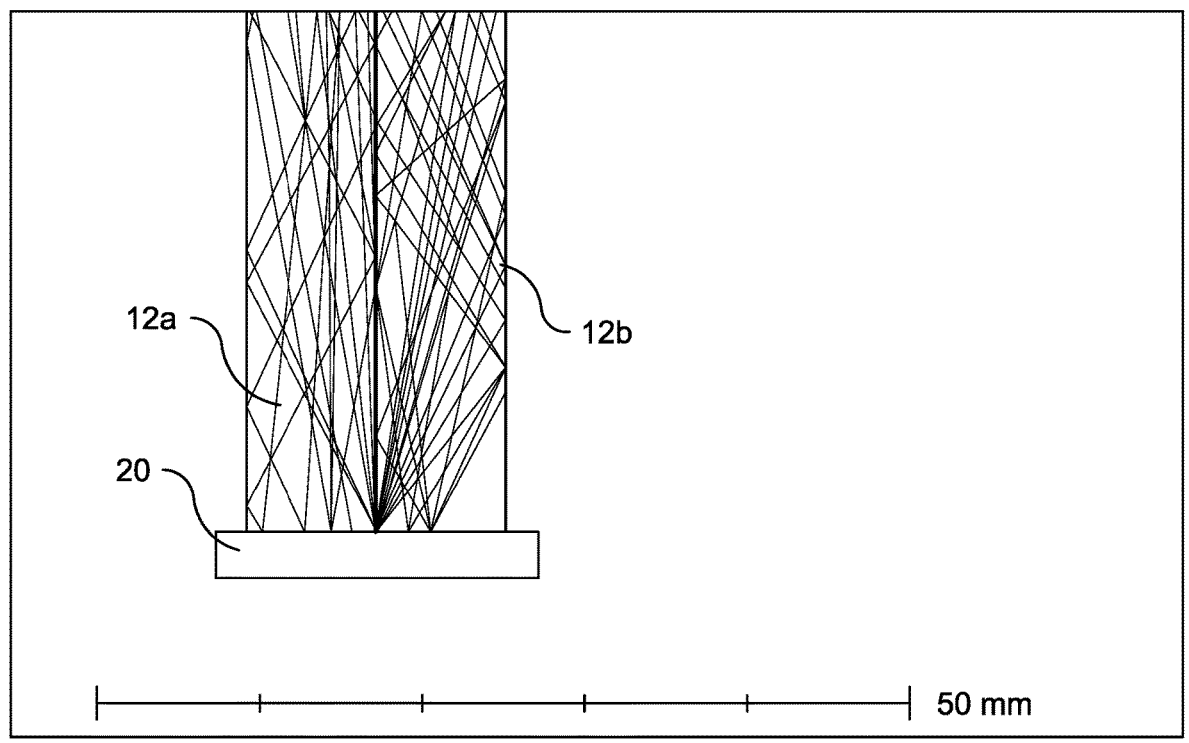
FIG. 11 is a magnified view of a portion of the schematic view shown in FIG. 10.

Photodetectors can be configured for use in this aspect of the presently disclosed technology in a variety of ways. For example, a filter or set of filters that in combination that matches the skin responsiveness curve can be incorporated into or used in conjunction with the photodetector cell, as illustrated in FIGS. 8-9B. An example of such a filter material is the UG11, manufactured by the Schott Group, which diminishes the responsivity to longer wavelength UV without affecting mid-UV or short UV regions of the spectrum. Interference filters can be constructed that selectively tune to pass certain wavelength regions, and reject (absorb) other regions to shape the response spectrum of the system (filters+photocell). Fluorescent materials that respond to UV radiation in a certain region of the UV can also be used to modify the spectral response of the system (such as $MgWO_4$ for erythema response spectrum) as described by Berger in *The sunburning ultraviolet meter: Design and performance*. Photochem. Photobiol. 1976:24; 587-593. Alternatively, the responsiveness of the photodetector cell's material can be selected to match the skin responsiveness curve, or the responsiveness of the photodetector cell can be electronically tuned to achieve this result. The combination of the photocell response spectrum and the modifying filters or intervening optical spectrum modifiers together as a unit can thus be made to respond with a signal similar to the way skin would respond to the incident light source.

In addition, the light source chosen for the measurement of the UV protectiveness of the sunscreen using the inventive device can have the same spectral distribution as the source that is used in clinical testing for the UVA-PF measurements. Thus the system can reproduce the UVA-PF of the sunscreen being tested by replicating the clinical test conditions with the same incident light spectrum, and using a detection system for the remitted light that responds with the same spectral response sensitivity as does human skin. Together, a simple two measurement observation sequence provides the UVA-PF of the sunscreen without requiring a spectral breakdown of the light into its individual wavelength components (monochromators or "spectral analyzer") in order to weight with skin response spectra and to determine a UVA-PF value.

The presently disclosed technology has been described in the context of calculating SPF and the likelihood that a composition will affect the biological responses of erythema, sunburn, or tanning. As will be readily appreciated by one skilled in the art, it is applicable in other photobiological contexts, such as the stimulation of melatonin production and the regulation of circadian rhythms.

It will be appreciated by those skilled in the art that changes could be made to the embodiments described above without departing from the broad inventive concept thereof. It is understood, therefore, that the presently disclosed technology is not limited to the particular embodiments disclosed, but it is intended to cover modifications within the spirit and scope of the presently disclosed technology as defined by the appended claims.

We claim:

1. A method of measuring the protection of a sunscreen composition, the method comprising:
exposing skin to a known intensity of light;
measuring the amount of remitted light from the skin;
applying sunscreen to the skin;

exposing the skin to which the sunscreen has been applied to the known intensity of emitted light;

measuring the amount of light remitted from the skin to which the sunscreen has been applied; and calculating an UltraViolet-A Protection Factor (UVA-PF) of the sunscreen by comparing the amount of light remitted from the skin with the sunscreen to the amount of light remitted from the skin without the sunscreen, wherein the light is emitted and measured by a light emission and sensing device having:

a light source;

an emitted light conduit for conducting the emitted light to the skin; and a remitted light conduit for conducting the light remitted from the skin to a photosensor, wherein the emitted light conduit and the remitted light conduit are in contact with a region of the skin, and are in contact with each other along a distance of at least 2 mm in the region at the surface of the skin.

2. The method of claim 1, wherein the light is polychromatic light.

3. The method of claim 1, wherein the light is polychromatic UVA light.

4. The method of claim 1, wherein the emitted light conduit and the remitted light conduit are separated by 10-40 microns.

5. The method of claim 4, wherein the emitted light conduit and the remitted light conduit are separated by 10-20 microns.

6. The method of claim 4, wherein the emitted light conduit and the remitted light conduit are in contact with the region of the skin, and are in contact with each other along a distance of at least 4 mm in the region at the surface of the skin.

7. The method of claim 1, wherein only the UVA-PF is measured.

8. The method of claim 1, wherein the broad spectrum skin protection factor (SPF) is measured.

9. The method of claim 1, wherein light source has the same spectral proportions to light sources used in clinical Protection Factor in UVA (PFA) evaluations, and shaping a response spectrum of a sensor to be similar to the human Persistent Pigment Darkening (PPD) action spectrum.

10. The method of claim 1, wherein the emitted light conduit and the remitted light conduit are in contact with the region of the skin, and are in contact with each other along a distance of at least 4 mm in the region at the surface of the skin.

11. The method of claim 10, wherein the emitted light conduit and the remitted light conduit are in contact with the region of the skin, and are in contact with each other along a distance of at least 8 mm in the region at the surface of the skin.

12. A device for measuring the protection of a sunscreen, the device comprising:

a light source for emitting light in the spectrum of light from which the sunscreen is intended to protect skin;

an emitted light conduit for conducting the emitted light to the skin; and a remitted light conduit for conducting the light remitted from the skin to a photosensor, wherein the emitted light conduit and the remitted light conduit are in contact with a region of the skin, and wherein the emitted light conduit and the remitted light conduit are in contact with each other along a distance of at least 2 mm in the region at the surface of the skin.

13. The device of claim 12, wherein the emitted light conduit and the remitted light conduit are separated by 10-40 microns.

14. The device of claim 13, wherein the emitted light conduit and the remitted light conduit are separated by 10-20 microns.

15. The device of claim 13, wherein the emitted light conduit and the remitted light conduit are in contact with the region of the skin, and are in contact with each other along a distance of at least 4 mm in the region at the surface of the skin.

16. The device of claim 12, wherein the emitted light conduit and the remitted light conduit are in contact with the region of the skin, and are in contact with each other along a distance of at least 4 mm in the region at the surface of the skin.

17. The device of claim 16, wherein the emitted light conduit and the remitted light conduit are in contact with the region of the skin, and are in contact with each other along a distance of at least 8 mm in the region at the surface of the skin.

18. A device for measuring sunscreen protection, the device comprising:

at least two optical conduits;

a cover sleeve surrounding the at least two optical conduits, the cover sleeve having a first end and an opposing second end;

a hub having a first end and an opposing second end, the second end of the hub being attached to the first end of the cover sleeve; and a light feed operatively connected to the first end of the hub, wherein each of the at least two optical conduits has a flat surface, the flat surface of one of the at least two optical conduits facing the flat surface of the other of the at least two optical conduits, wherein the at least two optical conduits include an emitted light conduit for conducting light emitted from the light feed to skin of a patient and a remitted light conduit for conducting light remitted from the skin to the light sensor, wherein the emitted light conduit and the remitted light conduit are separated by 10-40 microns, and wherein the at least two optical conduits are in contact with a region of the skin and in contact with each other along a distance of at least 2 mm in the region at the surface of the skin.

19. A method of measuring a protection value of sunscreen using a device having a first optical conduit and a second optical conduit, the first and second optical conduits being in contact with a region of skin and in contact with each other along a distance of at least 2 mm in the region at the surface of the skin, the method comprising:

emitting light through the first optical conduit to the skin; and receiving remitted light through the second optical conduit from the skin.

20. The method of claim 19, further comprising:

calculating an UltraViolet-A Protection Factor (UVA-PF) of the sunscreen by comparing the amount of light remitted from the skin with the sunscreen to the amount of light remitted from the skin without the sunscreen.

* * * * *